United States Patent
Wu et al.

(10) Patent No.: US 12,110,329 B2
(45) Date of Patent: Oct. 8, 2024

(54) ANTI-BTLA ANTIBODY

(71) Applicants: Shanghai Junshi Biosciences Co., Ltd., Shanghai (CN); Junmeng Biosciences Co., Ltd., Jiangsu (CN)

(72) Inventors: Hai Wu, Shanghai (CN); Jian Yao, Shanghai (CN); Sheng Yao, Shanghai (CN); Hui Feng, Shanghai (CN); Jing Zhang, Shanghai (CN); Yuehua Zhou, Jiangsu (CN)

(73) Assignees: Shanghai Junshi Biosciences Co., Ltd., Shanghai (CN); Junmeng Biosciences Co., Ltd., Jiangsu (CN)

( * ) Notice: Subject to any disclaimer, the term of this patent is extended or adjusted under 35 U.S.C. 154(b) by 736 days.

(21) Appl. No.: 17/164,597

(22) Filed: Feb. 1, 2021

(65) Prior Publication Data

US 2021/0246209 A1 Aug. 12, 2021

Related U.S. Application Data

(63) Continuation-in-part of application No. PCT/CN2019/098150, filed on Jul. 29, 2019.

(30) Foreign Application Priority Data

Aug. 2, 2018 (CN) .......................... 201810870514.0

(51) Int. Cl.
  *C07K 16/28* (2006.01)
  *A61K 39/00* (2006.01)
  *A61K 47/68* (2017.01)
  *A61P 35/00* (2006.01)
(52) U.S. Cl.
  CPC ...... *C07K 16/2818* (2013.01); *A61K 47/6803* (2017.08); *A61K 47/6849* (2017.08); *A61P 35/00* (2018.01); *A61K 2039/505* (2013.01); *C07K 2317/24* (2013.01); *C07K 2317/33* (2013.01); *C07K 2317/565* (2013.01); *C07K 2317/76* (2013.01); *C07K 2317/92* (2013.01)
(58) Field of Classification Search
  CPC combination set(s) only.
  See application file for complete search history.

(56) References Cited

U.S. PATENT DOCUMENTS

| | | |
|---|---|---|
| 2012/0288500 A1 | 11/2012 | Korman et al. |
| 2018/0118836 A1 | 5/2018 | Bernett et al. |
| 2018/0194855 A1* | 7/2018 | Harding ............. C07K 16/3023 |

FOREIGN PATENT DOCUMENTS

| | | |
|---|---|---|
| CN | 102762593 B | 10/2012 |
| CN | 105968189 A | 9/2016 |
| WO | 2008076560 A2 | 6/2008 |
| WO | 2010106051 A1 | 9/2010 |
| WO | 2011/014438 A1 | 2/2011 |
| WO | WO-2017062672 A2 * | 4/2017 ................ A61P 1/04 |
| WO | WO-2017096017 A1 * | 6/2017 ....... A61K 39/39558 |
| WO | 2017/144668 A1 | 8/2017 |

OTHER PUBLICATIONS

Kussie PH, Parhami-Seren B, Wysocki LJ, Margolies MN. J Immunol. Jan. 1, 1994;152(1):146-52. PMID: 8254187. (Year: 1994).*
Chen C, Roberts VA, Stevens S, Brown M, Stenzel-Poore MP, Rittenberg MB. EMBO J. Jun. 15, 1995;14(12):2784-94. doi: 10.1002/j.1460-2075.1995.tb07278.x. PMID: 7796805; PMCID: PMC398397. (Year: 1995).*
Sela-Culang I, Kunik V, Ofran Y. The structural basis of antibody-antigen recognition. Front Immunol. Oct. 8, 2013;4:302. doi: 10.3389/fimmu.2013.00302. PMID: 24115948; PMCID: PMC3792396. (Year: 2013).*
Janeway CA Jr., Travers P, Walport M, et al. Immunobiology: The Immune System in Health and Disease. 5th edition. New York: Garland Science; 2001. (Year: 2001).*
Lichtman MA. A Bacterial Cause of Cancer: An Historical Essay. Oncologist. May 2017;22(5):542-548. doi: 10.1634/theoncologist.2017-0007. Epub Apr. 21, 2017. PMID: 28432224; PMCID: PMC5423514. (Year: 2017).*
Wan Y, Li Y, Yan C, Yan M, Tang Z. Indole: A privileged scaffold for the design of anti-cancer agents. Eur J Med Chem. Dec. 1, 2019;183:111691. doi: 10.1016/j.ejmech.2019.111691. Epub Sep. 11, 2019. PMID: 31536895. (Year: 2019).*
Rashid HU, Xu Y, Muhammad Y, Wang L, Jiang J. Research advances on anticancer activities of matrine and its derivatives: An updated overview. Eur J Med Chem. Jan. 1, 2019;161:205-238. doi: 10.1016/j.ejmech.2018.10.037. Epub Oct. 19, 2018. PMID: 30359819. (Year: 2018).*
Garewal HS, Ramsey L, Kaugars G, Boyle J. Clinical experience with the micronucleus assay. J Cell Biochem Suppl. 1993;17F:206-12. doi: 10.1002/jcb.240531031. PMID: 8412196. (Year: 1993).*
Van Seventer JM, Hochberg NS. Principles of Infectious Diseases: Transmission, Diagnosis, Prevention, and Control. International Encyclopedia of Public Health. 2017:22-39. doi: 10.1016/B978-0-12-803678-5.00516-6. Epub Oct. 24, 2016. PMCID: PMC7150340. (Year: 2016).*

(Continued)

*Primary Examiner* — Adam Weidner
*Assistant Examiner* — Laura Ann Essex
(74) *Attorney, Agent, or Firm* — Kilpatrick Townsend & Stockton LLP

(57) ABSTRACT

The present invention relates to an anti-BTLA antibody or an antigen-binding fragment thereof comprising: at least one light chain CDR domain selected from SEQ ID NOs: 7, 8, 9, 10, 11, 12, 16, 17, 18, 22, 23, 24, 31, 32 and 33, and/or at least one heavy chain CDR domain selected from SEQ ID NOs: 1, 2, 3, 4, 5, 6, 13, 14, 15, 19, 20, 21, 25, 26, 27, 28, 29 and 30. The present invention also relates to a nucleic acid molecule encoding the antibody or the antigen-binding fragment thereof, a corresponding expression vector and a host cell, as well as therapeutic use of the antibody or the antigen-binding fragment thereof, the nucleic acid molecule, the expression vector and the host cell.

15 Claims, 5 Drawing Sheets

Specification includes a Sequence Listing.

(56) References Cited

OTHER PUBLICATIONS

Calder PC et al. Br J Nutr. May 2009;101 Suppl 1:S1-45. doi: 10.1017/S0007114509377867. PMID: 19586558. (Year: 2009).*

Cheng T, Bai J, Chung CS, Chen Y, Biron BM, Ayala A. Enhanced Innate Inflammation Induced by Anti-BTLA Antibody in Dual Insult Model of Hemorrhagic Shock/Sepsis. Shock. Jan. 2016;45(1):40-9. doi: 10.1097/SHK.0000000000000479. PMID: 26674453; PMCID: PMC4683612. (Year: 2016).*

Eissler et al., "Regulation of Myeloid Cells By activated T Cells Determines the Efficacy of PD-1 Blockade", Oncoimmunology, vol. 5, No. 12, Sep. 9, 2016, 12 pages.

Application No. EP19843756.8, Extended European Search Report, Mailed On Mar. 28, 2022, 9 pages.

Liu et al., "Distinct Changes of BTLA and HVEM Expressions in Circulating CD4+ and CD8+ T Cells in Hepatocellular Carcinoma Patients", Journal of Immunology Research, vol. 2018, Jul. 18, 2018, pp. 1-8.

Application No. IDP00202101545, Office Action, Mailed on Nov. 4, 2022, 6 pages.

SG11202100649V, "Search Report", Sep. 9, 2022, 4 pages.

Application No. SG11202100649V, Written Opinion, Mailed On Sep. 12, 2022, 10 pages.

Gertner-Dardene et al., "The co-receptor BTLA negatively regulates human Vγ9Vδ2 T-cell proliferation: a potential way of immune escape for lymphoma cells" Blood, Immubiology, Aug. 8, 2013, pp. 922-931, vol. 122, Issue 6.

Application PCT/CN2019/098150, Aug. 2, 2018, ISR/WO and translations, 19 pages.

* cited by examiner

SEQUENCE LISTING

```
<160> NUMBER OF SEQ ID NOS: 51

<210> SEQ ID NO 1
<211> LENGTH: 5
<212> TYPE: PRT
<213> ORGANISM: Artificial Sequence
<220> FEATURE:
<223> OTHER INFORMATION: HCDR1

<400> SEQUENCE: 1

Asp Thr Tyr Leu His
1               5

<210> SEQ ID NO 2
<211> LENGTH: 17
<212> TYPE: PRT
<213> ORGANISM: Artificial Sequence
<220> FEATURE:
<223> OTHER INFORMATION: HCDR2

<400> SEQUENCE: 2

Arg Ile Asp Pro Ala Asn Gly Asn Thr Lys Tyr Asp Pro Arg Phe Gln
1               5                   10                  15

Gly

<210> SEQ ID NO 3
<211> LENGTH: 10
<212> TYPE: PRT
<213> ORGANISM: Artificial Sequence
<220> FEATURE:
<223> OTHER INFORMATION: HCDR3

<400> SEQUENCE: 3

Asp Tyr Tyr Gly Ser Ser Leu Phe Asp Tyr
1               5                   10
```

```
<210> SEQ ID NO 4
<211> LENGTH: 5
<212> TYPE: PRT
<213> ORGANISM: Artificial Sequence
<220> FEATURE:
<223> OTHER INFORMATION: HCDR1

<400> SEQUENCE: 4

Asp Ser Tyr Ile His
1               5

<210> SEQ ID NO 5
<211> LENGTH: 17
<212> TYPE: PRT
<213> ORGANISM: Artificial Sequence
<220> FEATURE:
<223> OTHER INFORMATION: HCDR2

<400> SEQUENCE: 5

Arg Ile Asp Pro Ala Asn Gly Asn Thr Lys Tyr Asp Pro Lys Phe Arg
1               5                   10                  15
Gly

<210> SEQ ID NO 6
<211> LENGTH: 10
<212> TYPE: PRT
<213> ORGANISM: Artificial Sequence
<220> FEATURE:
<223> OTHER INFORMATION: HCDR3

<400> SEQUENCE: 6

Asp His Tyr Gly Ser Ser Leu Phe Asp Tyr
1               5                   10

<210> SEQ ID NO 7
<211> LENGTH: 16
<212> TYPE: PRT
<213> ORGANISM: Artificial Sequence
<220> FEATURE:
<223> OTHER INFORMATION: LCDR1

<400> SEQUENCE: 7

Lys Ser Ser Gln Ser Leu Leu Asp Ser Asp Gly Lys Thr Tyr Leu Asn
1               5                   10                  15

<210> SEQ ID NO 8
<211> LENGTH: 7
<212> TYPE: PRT
<213> ORGANISM: Artificial Sequence
<220> FEATURE:
<223> OTHER INFORMATION: LCDR2

<400> SEQUENCE: 8

Val Leu Ser Lys Leu Glu Ser
1               5

<210> SEQ ID NO 9
<211> LENGTH: 9
<212> TYPE: PRT
<213> ORGANISM: Artificial Sequence
<220> FEATURE:
<223> OTHER INFORMATION: LCDR3

<400> SEQUENCE: 9

Trp Gln Gly Thr His Phe Pro Tyr Thr
1               5
```

<210> SEQ ID NO 10
<211> LENGTH: 16
<212> TYPE: PRT
<213> ORGANISM: Artificial Sequence
<220> FEATURE:
<223> OTHER INFORMATION: LCDR1

<400> SEQUENCE: 10

Lys Ser Ser Gln Ser Leu Leu Asp Ser Asp Gly Lys Thr Tyr Leu Asn
1               5                   10                  15

<210> SEQ ID NO 11
<211> LENGTH: 7
<212> TYPE: PRT
<213> ORGANISM: Artificial Sequence
<220> FEATURE:
<223> OTHER INFORMATION: LCDR2

<400> SEQUENCE: 11

Leu Val Ser Lys Leu Asp Ser
1               5

<210> SEQ ID NO 12
<211> LENGTH: 9
<212> TYPE: PRT
<213> ORGANISM: Artificial Sequence
<220> FEATURE:
<223> OTHER INFORMATION: LCDR3

<400> SEQUENCE: 12

Trp Gln Gly Thr Tyr Phe Pro Tyr Thr
1               5

<210> SEQ ID NO 13
<211> LENGTH: 5
<212> TYPE: PRT
<213> ORGANISM: Artificial Sequence
<220> FEATURE:
<223> OTHER INFORMATION: HCDR1

<400> SEQUENCE: 13

His Thr Tyr Ala His
1               5

<210> SEQ ID NO 14
<211> LENGTH: 17
<212> TYPE: PRT
<213> ORGANISM: Artificial Sequence
<220> FEATURE:
<223> OTHER INFORMATION: HCDR2

<400> SEQUENCE: 14

Arg Ile Asp Pro Ala Asn Gly Asn Thr Lys Tyr Asp Pro Lys Phe Gln
1               5                   10                  15

Gly

<210> SEQ ID NO 15
<211> LENGTH: 10
<212> TYPE: PRT
<213> ORGANISM: Artificial Sequence
<220> FEATURE:
<223> OTHER INFORMATION: HCDR3

<400> SEQUENCE: 15

Asp His Tyr Gly Ser Ser Leu Leu Asp Tyr
1               5                   10

```
<210> SEQ ID NO 16
<211> LENGTH: 11
<212> TYPE: PRT
<213> ORGANISM: Artificial Sequence
<220> FEATURE:
<223> OTHER INFORMATION: LCDR1

<400> SEQUENCE: 16

Lys Ala Ser Gln Asp Ile Asn Lys Tyr Ile Ala
1               5                   10

<210> SEQ ID NO 17
<211> LENGTH: 7
<212> TYPE: PRT
<213> ORGANISM: Artificial Sequence
<220> FEATURE:
<223> OTHER INFORMATION: LCDR2

<400> SEQUENCE: 17

Tyr Thr Ser Thr Leu Gln Pro
1               5

<210> SEQ ID NO 18
<211> LENGTH: 13
<212> TYPE: PRT
<213> ORGANISM: Artificial Sequence
<220> FEATURE:
<223> OTHER INFORMATION: LCDR3

<400> SEQUENCE: 18

Leu Gln Tyr Ala Thr Tyr Ala Pro Pro Ala Val Ser Ile
1               5                   10

<210> SEQ ID NO 19
<211> LENGTH: 5
<212> TYPE: PRT
<213> ORGANISM: Artificial Sequence
<220> FEATURE:
<223> OTHER INFORMATION: HCDR1

<400> SEQUENCE: 19

Asp Thr Tyr Val His
1               5

<210> SEQ ID NO 20
<211> LENGTH: 17
<212> TYPE: PRT
<213> ORGANISM: Artificial Sequence
<220> FEATURE:
<223> OTHER INFORMATION: HCDR2

<400> SEQUENCE: 20

Arg Ile Asp Pro Ala Asn Gly His Thr Lys Phe Asp Pro Lys Phe Gln
1               5                   10                  15

Gly

<210> SEQ ID NO 21
<211> LENGTH: 10
<212> TYPE: PRT
<213> ORGANISM: Artificial Sequence
<220> FEATURE:
<223> OTHER INFORMATION: HCDR3

<400> SEQUENCE: 21

Asp Tyr Tyr Gly Ser Ser Leu Leu Asp Tyr
```

```
<210> SEQ ID NO 22
<211> LENGTH: 11
<212> TYPE: PRT
<213> ORGANISM: Artificial Sequence
<220> FEATURE:
<223> OTHER INFORMATION: LCDR1

<400> SEQUENCE: 22

Ser Glu Pro Pro Ser Glu Asp Gly Lys Thr Tyr
1               5                   10

<210> SEQ ID NO 23
<211> LENGTH: 3
<212> TYPE: PRT
<213> ORGANISM: Artificial Sequence
<220> FEATURE:
<223> OTHER INFORMATION: LCDR2

<400> SEQUENCE: 23

Val Val Ser
1

<210> SEQ ID NO 24
<211> LENGTH: 9
<212> TYPE: PRT
<213> ORGANISM: Artificial Sequence
<220> FEATURE:
<223> OTHER INFORMATION: LCDR3

<400> SEQUENCE: 24

Trp Gln Gly Thr His Phe Pro Tyr Thr
1               5

<210> SEQ ID NO 25
<211> LENGTH: 5
<212> TYPE: PRT
<213> ORGANISM: Artificial Sequence
<220> FEATURE:
<223> OTHER INFORMATION: HCDR1

<400> SEQUENCE: 25

Asp Thr Tyr Val His
1               5

<210> SEQ ID NO 26
<211> LENGTH: 17
<212> TYPE: PRT
<213> ORGANISM: Artificial Sequence
<220> FEATURE:
<223> OTHER INFORMATION: HCDR2

<400> SEQUENCE: 26

Arg Ile Asp Pro Ala Asn Gly His Thr Lys Tyr Asp Pro Lys Leu Gln
1               5                   10                  15

Gly

<210> SEQ ID NO 27
<211> LENGTH: 10
<212> TYPE: PRT
<213> ORGANISM: Artificial Sequence
<220> FEATURE:
<223> OTHER INFORMATION: HCDR3

<400> SEQUENCE: 27
```

```
Asp Tyr Tyr Gly Ser Ser Leu Leu Asp Tyr
1               5                   10
```

```
<210> SEQ ID NO 28
<211> LENGTH: 5
<212> TYPE: PRT
<213> ORGANISM: Artificial Sequence
<220> FEATURE:
<223> OTHER INFORMATION: HCDR1

<400> SEQUENCE: 28

Asp Thr Tyr Met His
1               5
```

```
<210> SEQ ID NO 29
<211> LENGTH: 17
<212> TYPE: PRT
<213> ORGANISM: Artificial Sequence
<220> FEATURE:
<223> OTHER INFORMATION: HCDR2

<400> SEQUENCE: 29

Arg Ile Asp Pro Ala Asn Gly Asn Thr Lys Phe Asp Pro Lys Phe Gln
1               5                   10                  15

Gly
```

```
<210> SEQ ID NO 30
<211> LENGTH: 10
<212> TYPE: PRT
<213> ORGANISM: Artificial Sequence
<220> FEATURE:
<223> OTHER INFORMATION: HCDR3

<400> SEQUENCE: 30

Asp His Tyr Gly Ser Ser Leu Leu Asp Tyr
1               5                   10
```

```
<210> SEQ ID NO 31
<211> LENGTH: 11
<212> TYPE: PRT
<213> ORGANISM: Artificial Sequence
<220> FEATURE:
<223> OTHER INFORMATION: LCDR1

<400> SEQUENCE: 31

Lys Ala Ser Gln Asp Ile Lys Ser Tyr Leu Ser
1               5                   10
```

```
<210> SEQ ID NO 32
<211> LENGTH: 7
<212> TYPE: PRT
<213> ORGANISM: Artificial Sequence
<220> FEATURE:
<223> OTHER INFORMATION: LCDR2

<400> SEQUENCE: 32

Tyr Ala Thr Ser Leu Ala Asp
1               5
```

```
<210> SEQ ID NO 33
<211> LENGTH: 13
<212> TYPE: PRT
<213> ORGANISM: Artificial Sequence
<220> FEATURE:
<223> OTHER INFORMATION: LCDR3

<400> SEQUENCE: 33
```

Leu Gln His Gly Ala Asp Ala Ala Pro Thr Val Ser Ile
1               5                   10

<210> SEQ ID NO 34
<211> LENGTH: 119
<212> TYPE: PRT
<213> ORGANISM: Artificial Sequence
<220> FEATURE:
<223> OTHER INFORMATION: Heavy chain variable region

<400> SEQUENCE: 34

Glu Val Gln Leu Gln Gln Ser Gly Ala Glu Leu Val Lys Pro Gly Ala
1               5                   10                  15

Ser Val Asn Leu Ser Cys Thr Ala Ser Gly Phe Ala Ile Arg Asp Thr
            20                  25                  30

Tyr Leu His Trp Val Lys Gln Arg Pro Glu Gln Val Leu Glu Trp Thr
        35                  40                  45

Gly Arg Ile Asp Pro Ala Asn Gly Asn Thr Lys Tyr Asp Pro Arg Phe
    50                  55                  60

Gln Gly Lys Ala Thr Leu Thr Ala Asp Thr Ser Ser Asn Thr Ala Tyr
65                  70                  75                  80

Leu His Leu Ser Ser Leu Thr Ser Glu Asp Thr Ala Val Tyr Tyr Cys
                85                  90                  95

Val Ala Asp Tyr Tyr Gly Ser Ser Leu Phe Asp Tyr Trp Gly Gln Gly
            100                 105                 110

Thr Thr Leu Thr Val Ser Ser
        115

<210> SEQ ID NO 35
<211> LENGTH: 119
<212> TYPE: PRT
<213> ORGANISM: Artificial Sequence
<220> FEATURE:
<223> OTHER INFORMATION: Heavy chain variable region

<400> SEQUENCE: 35

Glu Val Gln Leu Gln Gln Ser Gly Ala Glu Leu Val Lys Pro Gly Ala
1               5                   10                  15

Ser Val Lys Leu Ser Cys Thr Val Ser Gly Phe Asn Ile Lys Asp Ser
            20                  25                  30

Tyr Ile His Trp Val Lys Gln Arg Pro Glu Gln Gly Leu Glu Trp Ile
        35                  40                  45

Gly Arg Ile Asp Pro Ala Asn Gly Asn Thr Lys Tyr Asp Pro Lys Phe
    50                  55                  60

Arg Gly Lys Ala Thr Ile Thr Ala Asp Ala Ser Ser Asn Thr Ala Ala
65                  70                  75                  80

Leu Gln Val Ser Ser Leu Thr Ser Glu Asp Thr Ala Val Tyr Phe Cys
                85                  90                  95

Val Gly Asp His Tyr Gly Ser Ser Leu Phe Asp Tyr Trp Gly His Gly
            100                 105                 110

Thr Thr Leu Thr Val Ser Ser
        115

<210> SEQ ID NO 36
<211> LENGTH: 112
<212> TYPE: PRT
<213> ORGANISM: Artificial Sequence
<220> FEATURE:
<223> OTHER INFORMATION: Light chain variable region

<400> SEQUENCE: 36

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Val Leu Ser Lys Leu Glu Ser Gly Val Pro
    50                  55                  60

Asp Arg Phe Thr Gly Val Gly Ser Gly Thr Asp Phe Thr Leu Lys Ile
65                  70                  75                  80

Ser Arg Val Glu Ala Val Asp Leu Gly Val Tyr Tyr Cys Trp Gln Gly
                85                  90                  95

Thr His Phe Pro Tyr Thr Phe Gly Gly Gly Thr Lys Leu Glu Ile Lys
                100                 105                 110

<210> SEQ ID NO 37
<211> LENGTH: 112
<212> TYPE: PRT
<213> ORGANISM: Artificial Sequence
<220> FEATURE:
<223> OTHER INFORMATION: Light chain variable region

<400> SEQUENCE: 37

Glu Val Val Met Thr Gln Thr Pro Leu Thr Leu Ser Val Thr Ile Gly
1               5                   10                  15

Gln Ser Ala Ser Ile Ser Cys Lys Ser Ser Gln Ser Leu Leu Asp Ser
            20                  25                  30

Asp Gly Lys Thr Tyr Leu Asn Trp Phe Leu Gln Arg Pro Gly Gln Ser
        35                  40                  45

Pro Lys Arg Leu Met His Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Gly Val Glu Ala Glu Asp Leu Gly Val Tyr Tyr Cys Trp Gln Gly
                85                  90                  95

Thr Tyr Phe Pro Tyr Thr Phe Gly Gly Gly Thr Lys Leu Glu Thr Lys
                100                 105                 110

<210> SEQ ID NO 38
<211> LENGTH: 119
<212> TYPE: PRT
<213> ORGANISM: Artificial Sequence
<220> FEATURE:
<223> OTHER INFORMATION: Heavy chain variable region

<400> SEQUENCE: 38

Glu Val Gln Leu Gln Gln Ser Gly Ala Asp Leu Val Lys Pro Gly Ala
1               5                   10                  15

Ser Val Lys Leu Ser Cys Thr Ala Ser Gly Phe Asn Phe Lys His Thr
            20                  25                  30

Tyr Ala His Trp Val Lys Gln Arg Pro Glu Gly Leu Glu Trp Ile
        35                  40                  45

Gly Arg Ile Asp Pro Ala Asn Gly Asn Thr Lys Tyr Asp Pro Lys Phe
    50                  55                  60

Gln Gly Lys Ala Thr Met Thr Ala Asp Thr Ala Ser Asn Ala Ala Phe
65                  70                  75                  80

Leu Gln Leu Ser Ser Leu Thr Ser Glu Asp Thr Ala Val Tyr Tyr Cys
                85                  90                  95

Val Ala Asp His Tyr Gly Ser Ser Leu Leu Asp Tyr Trp Gly Gln Gly
            100                 105                 110

Thr Ser Leu Thr Val Ser Ser
        115

<210> SEQ ID NO 39
<211> LENGTH: 111
<212> TYPE: PRT
<213> ORGANISM: Artificial Sequence
<220> FEATURE:
<223> OTHER INFORMATION: Light chain variable region

<400> SEQUENCE: 39

Asp Ile Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile Asn Lys Tyr
            20                  25                  30

Ile Ala Trp Tyr Gln His Lys Pro Gly Lys Gly Pro Arg Leu Leu Ile
        35                  40                  45

His Tyr Thr Ser Thr Leu Gln Pro Gly Ile Pro Ser Arg Phe Ser Gly
    50                  55                  60

Ser Gly Ser Gly Ser Asp Tyr Ser Leu Thr Ile Ser Ser Leu Glu Ser
65                  70                  75                  80

Glu Asp Ser Ala Asn Tyr Tyr Cys Leu Gln Tyr Ala Thr Tyr Ala Pro
                85                  90                  95

Pro Ala Val Ser Ile Phe Gly Ala Gly Thr Lys Leu Glu Leu Lys
            100                 105                 110

<210> SEQ ID NO 40
<211> LENGTH: 119
<212> TYPE: PRT
<213> ORGANISM: Artificial Sequence
<220> FEATURE:
<223> OTHER INFORMATION: Heavy chain variable region

<400> SEQUENCE: 40

Glu Val Gln Leu Gln Gln Ser Gly Ala Asp Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Val His Trp Val Lys Gln Arg Pro Glu Gln Gly Leu Glu Trp Ile
        35                  40                  45

Gly Arg Ile Asp Pro Ala Asn Gly His Thr Lys Phe Asp Pro Lys Phe
    50                  55                  60

Gln Gly Lys Ala Thr Ile Thr Ala Asp Thr Ser Ser Asn Thr Ala Asn
65                  70                  75                  80

Leu Gln Ile Ser Ser Leu Thr Ser Glu Asp Thr Ala Val Tyr Tyr Cys
                85                  90                  95

Val Ser Asp Tyr Tyr Gly Ser Ser Leu Leu Asp Tyr Trp Gly Gln Gly
            100                 105                 110

Thr Thr Leu Thr Val Ser Ser
        115

<210> SEQ ID NO 41
<211> LENGTH: 108
<212> TYPE: PRT

<213> ORGANISM: Artificial Sequence
<220> FEATURE:
<223> OTHER INFORMATION: Light chain variable region

<400> SEQUENCE: 41

Asp Pro Asp Ser Thr His Phe Val Asp Tyr His Trp Thr Thr Cys Leu
1               5                   10                  15

His Leu Leu Gln Val Gln Ser Glu Pro Ser Glu Asp Gly Lys Thr
            20                  25                  30

Tyr Leu Ser Trp Ile Phe Gln Met Phe His Leu Ser Pro Lys Arg Leu
        35                  40                  45

Ile Tyr Val Val Ser Lys Leu Asn Ser Gly Val Pro Val Arg Leu Ser
50                  55                  60

Ala Asn His Ser Arg Thr Asp Phe Thr Leu Lys Ile Ser Arg Val Glu
65                  70                  75                  80

Ala Glu Asp Leu Gly Val Tyr Tyr Cys Trp Gln Gly Thr His Phe Pro
                85                  90                  95

Tyr Thr Phe Gly Gly Gly Thr Lys Leu Glu Ile Lys
            100                 105

<210> SEQ ID NO 42
<211> LENGTH: 119
<212> TYPE: PRT
<213> ORGANISM: Artificial Sequence
<220> FEATURE:
<223> OTHER INFORMATION: Heavy chain variable region

<400> SEQUENCE: 42

Glu Val Gln Leu Gln Gln Ser Gly Ala Glu Leu Val Arg Pro Gly Ala
1               5                   10                  15

Ser Val Lys Leu Ser Cys Thr Val Ser Gly Phe Asn Ile Lys Asp Thr
            20                  25                  30

Tyr Val His Trp Val Lys Gln Arg Pro Glu Gln Gly Leu Glu Trp Ile
        35                  40                  45

Gly Arg Ile Asp Pro Ala Asn Gly His Thr Lys Tyr Asp Pro Lys Leu
50                  55                  60

Gln Gly Thr Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Thr Asp Tyr Tyr Gly Ser Ser Leu Leu Asp Tyr Trp Gly Gln Gly
            100                 105                 110

Thr Thr Leu Thr Val Ser Ser
        115

<210> SEQ ID NO 43
<211> LENGTH: 119
<212> TYPE: PRT
<213> ORGANISM: Artificial Sequence
<220> FEATURE:
<223> OTHER INFORMATION: Heavy chain variable region

<400> SEQUENCE: 43

Glu Val His Leu Gln Gln Ser Gly Thr Glu Leu Met Lys Pro Gly Ala
1               5                   10                  15

Ser Val Lys Leu Ser Cys Thr Ala Ser Gly Leu Asn Ile Arg Asp Thr
            20                  25                  30

Tyr Met His Trp Val Lys Gln Arg Pro Glu Gln Gly Leu Glu Trp Ile
        35                  40                  45

Gly Arg Ile Asp Pro Ala Asn Gly Asn Thr Lys Phe Asp Pro Lys Phe
    50                  55                  60

Gln Gly Lys Ala Thr Leu Thr Ser Asp Thr Ser Ser Asn Thr Ala Tyr
65                  70                  75                  80

Leu His Phe Ser Ser Leu Thr Ser Glu Asp Ala Ala Val Tyr Tyr Cys
                85                  90                  95

Val Ser Asp His Tyr Gly Ser Ser Leu Leu Asp Tyr Trp Gly Gln Gly
                100                 105                 110

Thr Ser Leu Thr Val Ser Ser
            115

<210> SEQ ID NO 44
<211> LENGTH: 111
<212> TYPE: PRT
<213> ORGANISM: Artificial Sequence
<220> FEATURE:
<223> OTHER INFORMATION: Light chain variable region

<400> SEQUENCE: 44

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Lys Ser Tyr
                20                  25                  30

Leu Ser Trp Tyr Gln Gly Lys Pro Trp Lys Ser Pro Lys Thr Leu Ile
            35                  40                  45

Tyr Tyr Ala Thr Ser Leu Ala Asp Gly Val Pro Ser Arg Phe Ser Gly
        50                  55                  60

Ser Gly Ser Gly Gln Asp Tyr Ser Leu Thr Ile Thr Ser Leu Glu Ser
65                  70                  75                  80

Asp Asp Thr Ala Thr Tyr Tyr Cys Leu Gln His Gly Ala Asp Ala Ala
                85                  90                  95

Pro Thr Val Ser Ile Phe Gly Gly Gly Thr Lys Leu Glu Ile Lys
                100                 105                 110

<210> SEQ ID NO 45
<211> LENGTH: 119
<212> TYPE: PRT
<213> ORGANISM: Artificial Sequence
<220> FEATURE:
<223> OTHER INFORMATION: Heavy chain variable region

<400> SEQUENCE: 45

Gln Val Gln Leu Val Gln Ser Gly Ala Glu Val Lys Lys Pro Gly Ala
1               5                   10                  15

Ser Val Lys Leu Ser Cys Lys Ala Ser Gly Tyr Asn Phe Lys His Thr
                20                  25                  30

Tyr Ala His Trp Val Arg Gln Ala Pro Gly Gln Gly Leu Glu Trp Ile
            35                  40                  45

Gly Arg Ile Asp Pro Ala Asn Gly Asn Thr Lys Tyr Asp Pro Lys Phe
        50                  55                  60

Gln Gly Arg Ala Thr Met Thr Ala Asp Thr Ser Asn Thr Ala Tyr
65                  70                  75                  80

Leu Glu Leu Ser Ser Leu Arg Ser Glu Asp Thr Ala Val Tyr Tyr Cys
                85                  90                  95

Val Ala Asp His Tyr Gly Ser Ser Leu Leu Asp Tyr Trp Gly Gln Gly
                100                 105                 110

Thr Leu Val Thr Val Ser Ser

-continued

<210> SEQ ID NO 46
<211> LENGTH: 112
<212> TYPE: PRT
<213> ORGANISM: Artificial Sequence
<220> FEATURE:
<223> OTHER INFORMATION: Light chain variable region

<400> SEQUENCE: 46

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Phe Gln Gln Arg Pro Gly Gln Ser
        35                  40                  45

Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr Tyr Phe Pro Tyr Thr Phe Gly Gln Gly Thr Lys Leu Glu Ile Lys
            100                 105                 110

<210> SEQ ID NO 47
<211> LENGTH: 112
<212> TYPE: PRT
<213> ORGANISM: Artificial Sequence
<220> FEATURE:
<223> OTHER INFORMATION: Light chain variable region

<400> SEQUENCE: 47

Asp Val Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Phe Gln Gln Arg Pro Gly Gln Ser
        35                  40                  45

Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr Tyr Phe Pro Tyr Thr Phe Gly Gln Gly Thr Lys Leu Glu Ile Lys
            100                 105                 110

<210> SEQ ID NO 48
<211> LENGTH: 112
<212> TYPE: PRT
<213> ORGANISM: Artificial Sequence
<220> FEATURE:
<223> OTHER INFORMATION: Light chain variable region

<400> SEQUENCE: 48

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Phe Gln Gln Arg Pro Gly Gln Ser
            35                  40                  45

Pro Arg Leu Met His Leu Val Ser Lys Leu Asp Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr Tyr Phe Pro Tyr Thr Phe Gly Gln Gly Thr Lys Leu Glu Ile Lys
                100                 105                 110

<210> SEQ ID NO 49
<211> LENGTH: 384
<212> TYPE: DNA
<213> ORGANISM: Homo sapiens

<400> SEQUENCE: 49
aaagaatcat gtgatgtaca gctttatata aagagacaat ctgaacactc catcttagca      60
ggagatccct ttgaactaga atgccctgtg aaatactgtg ctaacaggcc tcatgtgact     120
tggtgcaagc tcaatggaac aacatgtgta aaacttgaag atagacaaac aagttggaag     180
gaagagaaga acatttcatt tttcattcta cattttgaac cagtgcttcc taatgacaat     240
gggtcatacc gctgttctgc aaattttcag tctaatctca ttgaaagcca ctcaacaact     300
ctttatgtga cagatgtaaa aagtgcctca gaacgaccct ccaaggacga aatggcaagc     360
agaccctggc tcctgtatag tgct                                            384

<210> SEQ ID NO 50
<211> LENGTH: 41
<212> TYPE: DNA
<213> ORGANISM: Artificial Sequence
<220> FEATURE:
<223> OTHER INFORMATION: Primer

<400> SEQUENCE: 50
gtacgctctt catgtaaaga atcatgtgat gtacagcttt a                          41

<210> SEQ ID NO 51
<211> LENGTH: 41
<212> TYPE: DNA
<213> ORGANISM: Artificial Sequence
<220> FEATURE:
<223> OTHER INFORMATION: Primer

<400> SEQUENCE: 51
gatcgctctt ctagcataca ggagccaggg tctgcttgcc a                          41

ANTI-BTLA ANTIBODY

CROSS REFERENCES TO RELATED APPLICATIONS

This application claims benefit and is a Continuation-in-part application of PCT Application No. PCT/CN2019/098150, filed Jul. 29, 2019, which claims priority to and the benefit of Chinese Patent Application No. 201810870514.0, filed on Aug. 2, 2018. Said PCT application and Chinese application are incorporated herein by reference in their entireties for all purposes.

REFERENCE TO A SEQUENCE LISTING

The Sequence Listing written in file 184868_ST25.txt created on Apr. 14, 2021, 24 KB, machine format IBM-PC, MS-Windows operating system, is hereby incorporated by reference in its entirety for all purposes.

REFERENCE TO A SEQUENCE LISTING

The Sequence Listing written in file 098903-1234654-000130US_Sequence Listing.txt, machine format IBM-PC, MS-Windows operating system, is hereby incorporated by reference in its entirety for all purposes.

TECHNICAL FIELD

The present invention belongs to the field of biotechnology, and specifically relates to an antibody or an antigen-binding fragment thereof that binds to BTLA and use thereof. More specifically, the present invention relates to an active antibody that recognizes human BTLA and can be used for the treatment or prevention of tumors, infectious diseases, inflammatory diseases, autoimmune diseases, and the like.

BACKGROUND

Positive and negative co-stimulatory signals play a crucial role in regulating the activity of B cells and T cells, and molecules that mediate these signals have been shown to be effective targets for immune modulators. In addition to the involvement of T cell receptor (TCR), positive co-stimulation is required for optimal activation of naive T cells, whereas negative co-stimulation is thought to be required for the acquisition of autoimmune tolerance and the termination of effector T cell function. Upon interacting with B7.1 or B7.2 on the surface of antigen-presenting cells (APCs), the prototype T-cell co-stimulatory molecule CD28 signals the promotion of T-cell proliferation and differentiation in response to the involvement of TCR, while CD28 homolog cytotoxic T-lymphocyte antigen-4 (CTLA-4) mediates the inhibition of T-cell proliferation and effector function (Chambers et al., *Ann. Rev. Immunol.*, 19: 565-594, 2001; Egen et al., *Nature Immunol.*, 3: 611-618, 2002). Several new molecules homologous to the B7 family have been found (Abbas et al., *Nat. Med.*, 5: 1345-6, 1999; Coyle et al., *Nat. Immunol.*, 2: 203-9, 2001; Carreno et al., *Annu. Rev. Immunol.*, 20: 29-53, 2002; Liang et al., *Curr. Opin. Immunol.*, 14: 384-90, 2002) and the elucidation for their roles in T cell activation just begins.

B and T lymphocyte attenuator (BTLA) is a member of the CD28 family, which also includes CD28, ICOS, CTLA-4 and PD-1. Based on the functional effect of increasing T cell proliferation by mAb addition, the first members of this family, CD28 and ICOS, were found to have an immune activation effect (Hutloff et al., 1999). And BTLA, CTLA-4, PD-1, and the like are described as negative regulatory proteins. Several in vivo studies have demonstrated the inhibitory effect of BTLA on lymphocyte responses. BTLA-deficient mice acquired by Murphy and his colleagues (Washington University St. Louis) showed a 3-fold increase in IgG production in response to T-dependent antigens. In addition, T cells and B cells isolated from BTLA-mice showed stronger proliferative responses to antigen-receptor stimulation with CD3- and anti-IgM, respectively (Watanabe, 2003). In an overexpression study, BTLA was found to associate with B cell receptor complexes as well as T cell receptors. In line with the results of this study, in BTLA-deficient lymphocytes, antigen-receptor independent stimulation using ConA (T cells) or LPS (B cells) was not affected and cannot be regulated even when using an anti-BTLA antibody. BTLA-knockout mice have been shown to develop spontaneous autoimmune diseases over time and to have a shortened lifespan (Oya, 2008). The disease severity increased for BTLA-knockout mice with experimental autoimmune encephalomyelitis (EAE) and allergic airway inflammation models, both of which rely on T cell activity (Watanabe, 2005; Deppong, 2006).

Herpesvirus entry mediator (HVEM) has been shown to be a ligand of BTLA (Scully et al, 2005). HVEM is a type I transmembrane glycoprotein with 4 extracellular cysteine-rich domains (CDRs) containing 6 pseudorepetitive cysteines, and it is a member of the TNF receptor superfamily. BTLA and HVEM regulate the function of T cells and APC mainly through dynamic expression on the cell surface. The binding of BTLA to ligand not only inhibits T cell proliferation and down-regulates the T cell activation marker CD25, but also inhibits the production of IFN-γ, IL-2, IL-4, IL-10, and the like, but does not induce cell apoptosis. The binding of HVEM to BTLA results in the down-regulation of T cell activation and proliferation (Sedy, 2005). These findings indicate that BTLA expression or BTLA-HVEM binding is strongly correlated with T cell activation and proliferation.

An antibody can be used as a therapeutic agent. Some antibodies may cause unwanted immunogenicity of the antibody when used as therapeutic agents in vivo. Repeated use of a monoclonal antibody in humans results in an immune response against the therapeutic antibody (e.g., human anti-mouse antibody or HAMA), due to the rodent origin of the most monoclonal antibodies. Such immune responses result in at least a loss of therapeutic efficacy and, at most, a potentially lethal allergic reaction. One method for reducing the immunogenicity of rodent antibodies includes producing chimeric antibodies, in which the mouse variable region (Fv) is fused to the human constant region (Liu et al. (1987) *Proc. Natl. Acad. Sci. USA* 84: 3439-43). However, mice injected with a hybrid of the human variable region and the mouse constant region develop a strong antibody response against the human variable region, suggesting that the retention of the intact rodent Fv region in such chimeric antibodies may still cause deleterious immunogenicity in patients.

In addition, grafting of the complementarity determining region (CDR) loops of the rodent variable domain onto the human framework (i.e., humanization) has been used to further minimize rodent sequences. Jones et al. (1986) *Nature* 321: 522; Verhoeyen et al. (1988) *Science* 239: 1534. However, CDR loop exchange still fails to uniformly produce an antibody with the same binding properties as the initial antibody. In humanized antibodies, changes in framework residues (FRs) (residues involved in CDR loop support) are often required to maintain the antigen-binding affinity. Kabat et al. (1991) *J. Immunol.* 147: 1709. Although the use of CDR grafting and framework residue retention in many humanized antibody constructs has been reported, it is difficult to predict whether a particular sequence will produce an antibody with the desired binding properties and, occasionally, biological properties. See, e.g., Queen et al., (1989) *Proc. Natl. Acad. Sci. USA* 86: 10029; Gorman et al., (1991) *Proc. Natl. Acad. Sci. USA* 88: 4181; and Hodgson, (1991) *Biotechnology* (NY), 9: 421-5. Furthermore, in most of the existing studies, different human sequences are adopted for the light and heavy chain variable sequences of animals, rendering the predictability of such studies questionable. The sequences of known antibodies, or more generally antibodies having a known X-ray crystal structure such as antibodies NEW and KOL, have been used. See, e.g., Jones et al., supra; Verhoeyen et al., supra; and Gorman et al., supra. Exact sequence information has been reported for a few humanized constructs.

There is a need for anti-BTLA antibodies, particularly anti-BTLA monoclonal antibodies, for use in the treatment of human disorders (e.g., inflammatory disorders, autoimmune disorders, and proliferative disorders). Such antibodies may preferably have low immunogenicity in human subjects, allowing repeated administration without adverse immune responses.

SUMMARY OF INVENTION

The present invention relates to one or more anti-human BTLA antibodies or antigen-binding fragments thereof, and the use of the antibodies or the antigen-binding fragments thereof in treating diseases.

In one or more embodiments, the present invention relates to an isolated antibody or an antigen-binding fragment thereof that specifically binds to human BTLA (B- and T-lymphocyte attenuator), comprising one or more properties selected from the following:
 A) blocking the binding of BTLA to HVEM (herpesvirus entry mediator);
 B) cross-reacting with cynomolgus monkey BTLA;
 C) binding to human BTLA with a $K_D \leq 0.28$ nM; and
 D) having no ability to mediate ADCC effect.

In one or more embodiments, the present invention relates to an isolated antibody or an antigen-binding fragment thereof that binds to human BTLA comprising at least one light chain CDR domain selected from SEQ ID NOs: 7, 8, 9, 10, 11, 12, 16, 17, 18, 22, 23, 24, 31, 32 and 33, and at least one heavy chain CDR domain selected from SEQ ID NOs: 1, 2, 3, 4, 5, 6, 13, 14, 15, 19, 20, 21, 25, 26, 27, 28, 29 and 30.

In one or more embodiments, the present invention relates to an isolated antibody or an antigen-binding fragment thereof that binds to human BTLA, wherein the amino acid sequences of the CDR1, CDR2, and CDR3 of the light chain CDR are selected from any one of the following groups A-E:

| Group | LCDR1 | LCDR2 | LCDR3 |
|---|---|---|---|
| A | SEQ ID NO: 7 | SEQ ID NO: 8 | SEQ ID NO: 9 |
| B | SEQ ID NO: 10 | SEQ ID NO: 11 | SEQ ID NO: 12 |
| C | SEQ ID NO: 16 | SEQ ID NO: 17 | SEQ ID NO: 18 |
| D | SEQ ID NO: 22 | SEQ ID NO: 23 | SEQ ID NO: 24 |
| E | SEQ ID NO: 31 | SEQ ID NO: 32 | SEQ ID NO: 33 | and/or the amino acid sequences of the CDR1, CDR2 and CDR3 of the heavy chain CDR are selected from any one of the following groups F-K:

| Group | HCDR1 | HCDR2 | HCDR3 |
|---|---|---|---|
| F | SEQ ID NO: 1 | SEQ ID NO: 2 | SEQ ID NO: 3 |
| G | SEQ ID NO: 4 | SEQ ID NO: 5 | SEQ ID NO: 6 |
| H | SEQ ID NO: 13 | SEQ ID NO: 14 | SEQ ID NO: 15 |
| I | SEQ ID NO: 19 | SEQ ID NO: 20 | SEQ ID NO: 21 |
| G | SEQ ID NO: 25 | SEQ ID NO: 26 | SEQ ID NO: 27 |
| K | SEQ ID NO: 28 | SEQ ID NO: 29 | SEQ ID NO: 30 |

In one or more embodiments, the present invention relates to an isolated antibody or an antigen-binding fragment thereof that binds to human BTLA, wherein the amino acid sequences of the CDR1, CDR2 and CDR3 of the heavy chain CDR and the amino acid sequences of the CDR1, CDR2 and CDR3 of the light chain CDR are selected from any one of the following groups I-IX:

| Group | LCDR1 | LCDR2 | LCDR3 | HCDR1 | HCDR2 | HCDR3 |
|---|---|---|---|---|---|---|
| I | SEQ ID NO: 7 | SEQ ID NO: 8 | SEQ ID NO: 9 | SEQ ID NO: 1 | SEQ ID NO: 2 | SEQ ID NO: 3 |
| II | SEQ ID NO: 10 | SEQ ID NO: 11 | SEQ ID NO: 12 | SEQ ID NO: 4 | SEQ ID NO: 5 | SEQ ID NO: 6 |
| III | SEQ ID NO: 16 | SEQ ID NO: 17 | SEQ ID NO: 18 | SEQ ID NO: 13 | SEQ ID NO: 14 | SEQ ID NO: 15 |
| IV | SEQ ID NO: 22 | SEQ ID NO: 23 | SEQ ID NO: 24 | SEQ ID NO: 19 | SEQ ID NO: 20 | SEQ ID NO: 21 |
| V | SEQ ID NO: 22 | SEQ ID NO: 23 | SEQ ID NO: 24 | SEQ ID NO: 25 | SEQ ID NO: 26 | SEQ ID NO: 27 |
| VI | SEQ ID NO: 31 | SEQ ID NO: 32 | SEQ ID NO: 33 | SEQ ID NO: 28 | SEQ ID NO: 29 | SEQ ID NO: 30 |
| VII | SEQ ID NO: 7 | SEQ ID NO: 8 | SEQ ID NO: 9 | SEQ ID NO: 4 | SEQ ID NO: 5 | SEQ ID NO: 6 |
| VIII | SEQ ID NO: 10 | SEQ ID NO: 11 | SEQ ID NO: 12 | SEQ ID NO: 1 | SEQ ID NO: 2 | SEQ ID NO: 3 |
| IX | SEQ ID NO: 10 | SEQ ID NO: 11 | SEQ ID NO: 12 | SEQ ID NO: 13 | SEQ ID NO: 14 | SEQ ID NO: 15 |

In one or more embodiments, the present invention relates to an isolated antibody or an antigen-binding fragment thereof that binds to human BTLA comprising a light chain variable region and a heavy chain variable region, wherein the amino acid sequence of the light chain variable region is selected from SEQ ID NOs: 36, 37, 39, 41, 44, 46, 47 and 48, and the amino acid sequence of the heavy chain variable region is selected from SEQ ID NOs: 34, 35, 38, 40, 42, 43 and 45.

In one or more embodiments, the present invention relates to an isolated antibody or an antigen-binding fragment thereof that binds to human BTLA, wherein the amino acid sequence of the light chain variable region is set forth in SEQ ID NO: 36, and the amino acid sequence of the heavy chain variable region is set forth in SEQ ID NO: 34.

In one or more embodiments, the present invention relates to an isolated antibody or an antigen-binding fragment thereof that binds to human BTLA, wherein the amino acid sequence of the light chain variable region is set forth in SEQ ID NO: 36, and the amino acid sequence of the heavy chain variable region is set forth in SEQ ID NO: 35.

In one or more embodiments, the present invention relates to an isolated antibody or an antigen-binding fragment thereof that binds to human BTLA, wherein the amino acid sequence of the light chain variable region is set forth in SEQ ID NO: 37; and the amino acid sequence of the heavy chain variable region is set forth in SEQ ID NO: 34.

In one or more embodiments, the present invention relates to an isolated antibody or an antigen-binding fragment thereof that binds to human BTLA, wherein the amino acid sequence of the light chain variable region is set forth in SEQ ID NO: 37, and the amino acid sequence of the heavy chain variable region is set forth in SEQ ID NO: 35.

In one or more embodiments, the present invention relates to an isolated antibody or an antigen-binding fragment thereof that binds to human BTLA, wherein the amino acid sequence of the light chain variable region is set forth in SEQ ID NO: 39, and the amino acid sequence of the heavy chain variable region is set forth in SEQ ID NO: 38.

In one or more embodiments, the present invention relates to an isolated antibody or an antigen-binding fragment thereof that binds to human BTLA, wherein the amino acid sequence of the light chain variable region is set forth in SEQ ID NO: 41, and the amino acid sequence of the heavy chain variable region is set forth in SEQ ID NO: 40.

In one or more embodiments, the present invention relates to an isolated antibody or an antigen-binding fragment thereof that binds to human BTLA, wherein the amino acid sequence of the light chain variable region is set forth in SEQ ID NO: 41, and the amino acid sequence of the heavy chain variable region is set forth in SEQ ID NO: 42.

In one or more embodiments, the present invention relates to an isolated antibody or an antigen-binding fragment thereof that binds to human BTLA, wherein the amino acid sequence of the light chain variable region is set forth in SEQ ID NO: 44, and the amino acid sequence of the heavy chain variable region is set forth in SEQ ID NO: 43.

In one or more embodiments, the present invention relates to an isolated antibody or an antigen-binding fragment thereof that binds to human BTLA, wherein the amino acid sequence of the light chain variable region is set forth in SEQ ID NO: 46, and the amino acid sequence of the heavy chain variable region is set forth in SEQ ID NO: 45.

In one or more embodiments, the present invention relates to an isolated antibody or an antigen-binding fragment thereof that binds to human BTLA, wherein the amino acid sequence of the light chain variable region is set forth in SEQ ID NO: 47, and the amino acid sequence of the heavy chain variable region is set forth in SEQ ID NO: 45.

In one or more embodiments, the present invention relates to an isolated antibody or an antigen-binding fragment thereof that binds to human BTLA, wherein the amino acid sequence of the light chain variable region is set forth in SEQ ID NO: 48, and the amino acid sequence of the heavy chain variable region is set forth in SEQ ID NO: 45.

In one or more embodiments, the isolated antibody or the antigen-binding fragment thereof disclosed herein that binds to human BTLA is an IgG type, more preferably an IgG4 subtype.

In one or more embodiments, the isolated antibody or the antigen-binding fragment thereof disclosed herein that binds to human BTLA is a single chain Fv antibody; in some embodiments, the antibody or the antigen-binding fragment thereof is a Fab antibody; in some embodiments, the antibody or the antigen-binding fragment thereof is an Fab' antibody; and in some embodiments, the antibody or the antigen-binding fragment thereof is an (Fab')$_2$ antibody.

In other embodiments, the present invention relates to an isolated polypeptide comprising the VL domain or the VH domain of any one of the antibodies or the antigen-binding fragments thereof described herein.

In other embodiments, the present invention relates to an isolated nucleic acid encoding the VL domain or the VH domain of any one of the antibodies or the antigen-binding fragments thereof described herein.

In other embodiments, the present invention relates to a composition comprising one or more of the antibodies or the antigen-binding fragments thereof described herein and a pharmaceutically acceptable carrier or diluent.

In other embodiments, the present invention relates to a method for preventing or treating diseases by eliminating, inhibiting, or reducing BTLA activity using one or more of the antibodies or the antigen-binding fragments thereof described herein, comprising administering to a subject in need thereof a therapeutically effective amount of the antibody or the antigen-binding fragment thereof, the nucleic acid, the expression vector, the host cell, the immunoconjugate, or the pharmaceutical composition disclosed herein. Preferably, the prevention or treatment of the diseases or disorders is benefited by the elimination, inhibition, or reduction of BTLA activity; preferably, the diseases or disorders are selected from cancers, infectious diseases and inflammatory diseases.

In other embodiments, the present invention also relates to use of the antibody or the antigen-binding fragment, the nucleic acid, the expression vector, the host cell, the immunoconjugate, or the pharmaceutical composition for preparing a medicament for treating or preventing diseases or disorders, preferably BTLA-mediated diseases, which may be selected from cancers, infectious diseases or inflammatory diseases.

DETAILED DESCRIPTION

Figure 1:
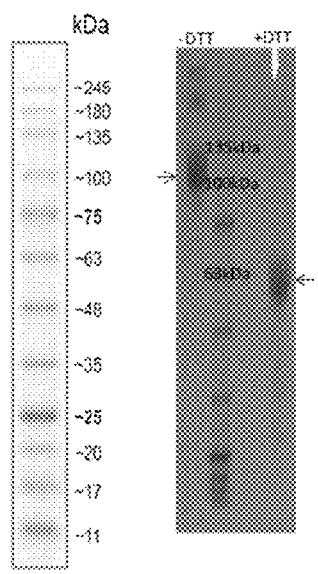
FIG. 1 shows the SDS-PAGE electropherogram of the human BTLA extracellular domain protein.

The mammalian immune system has developed several pathways that control the potentially deleterious activity of T and B lymphocytes, including various cytokine-receptor pathways and co-stimulatory pathways involving receptors (such as CD28, CTLA-4, PD-1, and BTLA). The CD28-B7 interaction is an example of a positive co-stimulatory pathway (i.e., CD28 triggers an increase in T cell response to antigen-specific triggers), while the other 3 receptors are inhibitory co-stimulatory pathways. CTLA-4, PD-1, and BTLA show overlapping but unique expression profiles and limit the activity of T and B lymphocytes and other immune cells (see Deppong et al., *J. Immunol* 2006; Tao et al., *J. Immunol* 2005). Although CTLA-4 competes with CD28 for binding to B7.1 and B7.2 (CD80 and CD86) and sets an initial threshold for the naive T cell activation in lymph nodes and spleen, PD-1 and BTLA each have their own unique ligands (PD-L1/-L2 and HVEM, respectively) and appear to control peripheral T cell homeostasis and reactivation (see Krieg et al., *Nat. Immunol* 2007).

BTLA down regulates the activation of B cells and T cells. As its name suggests, B and T lymphocyte attenuator (BTLA) is expressed on both resting and activated B and T lymphocytes. BTLA is a type I transmembrane glycoprotein with a cytoplasmic tail containing several tyrosine-inhibiting motifs (Watanabe, 2003). BTLA shares a certain structural similarity with the members of the CD28/CTLA-4 family, but it has unique properties. BTLA is associated with a variety of immunological, inflammatory, and proliferative diseases. Therefore, the development of monoclonal antibodies capable of blocking the human BTLA-HVEM binding is a continuing need for disease treatment.

Definitions

In order that the present invention can be more readily understood, some technical and scientific terms are specifically defined as follows. Unless otherwise defined herein, all other technical and scientific terms used herein have the same meaning as commonly understood by one of ordinary skill in the art to which the present invention belongs.

Herein, unless otherwise or specifically specified in the context, "activation", "stimulation," and "treatment" for a cell or a receptor may have the same meaning. For example, the cell or the receptor is activated, stimulated, or treated with a ligand. "Ligands" include natural and synthetic ligands, such as cytokines, cytokine variants, analogs, mutant proteins, and binding compounds derived from antibodies. "Ligands" also include small molecules, such as peptidomimetics of cytokines and peptidomimetics of antibodies. "Activation" may refer to the activation of a cell regulated by internal mechanisms as well as external or environmental factors. "Response/reaction", e.g., a response of a cell, a tissue, an organ, or an organism, includes changes in biochemical or physiological behaviors (e.g., concentration, density, adhesion or migration, gene expression rate, or differentiation state within a biological compartment), where the changes are associated with an activation, a stimulation or a treatment, or are associated with an internal mechanism such as genetic programming.

"Activity" of a molecule may describe or refer to the binding of the molecule to a ligand or a receptor; the catalytic activity; the ability of stimulating gene expression or cell signaling, differentiation or maturation; the antigenic activity; the regulation of the activity of other molecules, etc. "Activity" of a molecule may also refer to activity in the regulation or maintenance of the cell-cell interaction (e.g., adhesion), or in the maintenance of cellular structure (e.g., cell membrane or cell skeleton). "Activity" may also refer to specific activity, such as [catalytic activity]/[mg protein], [immunological activity]/[mg protein], or concentration in a biological compartment, etc. "Activity" may refer to the regulation of a component of the innate immune system or the adaptive immune system. "Proliferative activity" includes activities that promote, are necessary for, or are specifically associated with aspects such as normal cell division, as well as cancers, tumors, dysplasia, cell transformation, metastasis, and angiogenesis.

"Administration" and "treatment" as applied to an animal, human, subject, cell, tissue, organ, or biological fluid mean contacting an exogenous drug, therapeutic agent, diagnostic agent, or composition with the animal, human, subject, cell, tissue, organ, or biological fluid. "Administration" and "treatment" may refer to, for example, therapeutic, pharmacokinetic, diagnostic, research, and experimental methods. The treatment of cells includes contacting an agent with the cells and contacting the agent with a fluid which contacts the cells. "Administration" and "treatment" also mean in vitro and ex vivo treatments, e.g., in vitro and ex vivo treatments of a cell with an agent, a diagnosis, a binding compound, or another cell. "Treatment" also includes administering a therapeutic agent, e.g., a composition comprising any of the antibodies or the antigen-binding fragments thereof disclosed herein, internally or externally to a patient in need. In general, the antibodies or the antigen-binding fragments thereof or corresponding pharmaceutical compositions described herein are administered in an amount effective to alleviate one or more symptoms of the disease in the patient or population being treated, whether by inducing regression or inhibiting progression of these symptoms to any clinically measurable degree. An amount of therapeutic agent effective to alleviate any particular disease symptom (also referred to as a "therapeutically effective amount") may vary depending on factors such as the disease state, age, and weight of a patient, and the ability of the agent to elicit a desired reaction in the patient. Whether a symptom of a disease is alleviated can be assessed by any clinical measurements commonly performed by physicians or other healthcare providers to assess the severity or progression of a symptom.

The term "subject" or "patient" includes any organism, preferably an animal, more preferably a mammal (such as rat, mouse, dog, cat, rabbit), and most preferably a human.

Herein, "administration" or "treatment" can be accomplished by an invasive route, e.g., by an injection administration of any of the anti-BTLA antibodies or antigen-binding fragments thereof, or corresponding pharmaceutical compositions thereof described herein. Administration by non-invasive routes (e.g., oral administration; e.g., oral administration in pills, capsules, or tablets) is also within the scope of the present invention. In one embodiment of the present invention, the anti-BTLA antibody or the antigen-binding fragment thereof, or a pharmaceutical composition thereof is administered intravenously, subcutaneously, intramuscularly, intra-arterially, intra-articularly (e.g., in arthritic joints), by inhalation, by aerosol delivery, or intratumorally.

Any one of the anti-BTLA antibodies or the antigen-binding fragments thereof, or corresponding compositions thereof described herein can be administered using medical devices known in the art. For example, the pharmaceutical composition disclosed herein may be administered by injection using a hypodermic needle; or the pharmaceutical composition disclosed herein may be administered by injection using an intravenous needle.

In some embodiments, any one of the anti-BTLA antibodies or the antigen-binding fragments thereof, or corresponding pharmaceutical compositions thereof described herein can be used alone or in combination to treat or prevent any disease or condition in a subject in need of such a treatment or prevention.

Herein, the terms "B and T lymphocyte attenuator" and "BTLA" gene/protein can be used interchangeably and include variants, isotypes, homologues, orthologs, and paralogs. For example, in some embodiments, a human BTLA-specific antibody can cross-react with BTLA from a non-human species. In other embodiments, a human BTLA-specific antibody may be fully specific for human BTLA and not have species cross-reactivity or other types of cross-reactivities. Unless otherwise stated, the term "human BTLA" or "hBTLA" refers to the human BTLA sequence. Unless otherwise stated, the human BTLA sequence includes all human isotypes and BTLA variants, e.g., the complete amino acid sequence of human BTLA with Genbank accession No. AAP44003. There are also at least two human BTLA transcript variants, transcript variant 1 and transcript variant 2. The former encodes a protein that is 289 amino acids in length (GenBank accession No. NP_861445) and has nearly 98% identity to the BTLA sequence with an accession No. AAP44003, and the latter encodes a protein that is 241 amino acids in length (GenBank accession No. NP_001078826).

BTLA is a negative regulator of immune response with a C-terminal inhibitory motif involved in the inhibition of IL-2 production and T cell expansion (Watanabe et al., *Nat. Immunol.*, 4, 670-679, 2003; Chemnitz et al, *J. Immunol.*, 176, 6603-6614, 2006). In addition, human BTLA can be an epitope in the extracellular domain of BTLA that specifically binds to the antibody disclosed herein.

The extracellular nucleotide sequence of a specific BTLA sequence may generally have at least 90% identity to the human BTLA extracellular domain set forth in SEQ ID NO: 49 or the nucleotide sequence of other isotypes, and contain amino acid residues identified as the amino acid sequence of human when compared to BTLA amino acid sequences of other species (e.g., murine). In some cases, the human BTLA extracellular domain may have at least 95%, or even at least 96%, 97%, 98% or 99% identity to human BTLA extracellular domain set forth in SEQ ID NO: 49, or other isotypes or variants.

The term "immune response" refers to the action of, such as lymphocytes, antigen-presenting cells, phagocytes, granulocytes, and soluble macromolecules produced by the above cells or liver (including antibodies, cytokines, and complement), which results in the selective damage, destruction, or elimination of cells or tissues invaded by or infected with pathogens, cancerous cells, or normal human cells or tissues in the case of autoimmunity or pathological inflammation from the body.

As used herein, the term "antibody" refers to any form of antibodies having a desired bioactivity. Thus, it is used in the broadest sense and specifically includes, but is not limited to, monoclonal antibodies (including full length monoclonal antibodies), polyclonal antibodies, multispecific antibodies (e.g., bispecific antibodies), humanized antibodies, fully human antibodies, chimeric antibodies, and camelized single domain antibodies. As used herein, the term "anti-BTLA antibody" or "antigen-binding fragment" of the antibody refers to an antibody that binds to BTLA and blocks the binding of BTLA to HVEM, including fragments or derivatives of the antibody, typically including at least one fragment of an antigen-binding region or an variable region (e.g., one or more CDRs) of the antibody, which retains at least some binding specificities of the antibody. Examples of antibody binding fragments include, but are not limited to, Fab, Fab', F(ab')$_2$, and Fv fragments; diabodies; linear antibodies; single chain antibody molecules, such as sc-Fv; nanobodies and multispecific antibodies formed from antibody fragments. A binding fragment or a derivative typically retains at least 10% of its BTLA binding activity when the BTLA binding activity is expressed on a molar concentration basis. Preferably, a binding fragment or a derivative retains at least 20%, 50%, 70%, 80%, 90%, 95%, or 100% or more of the BTLA binding affinity of the antibody. It is also contemplated that anti-BTLA antigen-binding fragments may include conservative or non-conservative amino acid substitutions (referred to as "conservative variants" or "function-conservative variants" of antibodies) that do not significantly alter their biological activity.

The term "isolated antibody" refers to the purified state of an antibody or an antigen-binding fragment thereof, and in this case means that the molecule is substantially free of other biomolecules, such as nucleic acids, proteins, lipids, sugars, or other substances such as cell debris and growth media. The term "isolated" does not mean the complete absence of such substances or the absence of water, buffers, or salts, unless they are present in an amount that significantly interferes with the experimental or therapeutic use of the antibodies or the antigen-binding fragments thereof described herein.

As used herein, the term "functional fragment" or "antigen-binding fragment" refers in particular to an antibody fragment such as an Fv, an scFv, a Fab, an F(ab')$_2$, an Fab', an scFv-Fc fragment or a diabody, or any fragment capable of increasing half-life by chemical modification, e.g. addition of poly(alkylene)glycol such as polyethylene glycol ("PEGylation") (PEGylated fragments known as Fv-PEG, scFv-PEG, Fab-PEG, F(ab')$_2$-PEG or Fab'-PEG) ("PEG" being polyethylene glycol), or by incorporation into liposomes, and the fragment has EGFR binding activity. Preferably, the functional fragment consists of or comprises a part of the sequence of the heavy or light variable chain of the antibody from which it is derived, which is sufficient to retain the same binding specificity and sufficient affinity as the antibody from which it is derived, which, for BTLA, is preferably at least 1/100, and more preferably at least 1/10 of the affinity of the antibody from which it is derived. Such functional fragments will comprise at least 5 amino acids, preferably 10, 15, 25, 50 and 100 contiguous amino acids of the antibody sequence from which they are derived.

A "Fab fragment" consists of a light chain, a CH1 and a variable region of a heavy chain. The heavy chain of a Fab molecule cannot form a disulfide bond with another heavy chain molecule.

An "Fc" region contains 2 heavy chain fragments comprising the CH1 and CH2 domains of an antibody. The 2 heavy chain fragments are held together by two or more disulfide bonds and by the hydrophobic interaction of the CH3 domains.

An "Fab' fragment" contains a light chain and a heavy chain portion or fragment comprising the VH domain, the CH1 domain and the region between the CH1 and CH2 domains, such that interchain disulfide bonds can be formed between 2 heavy chains of 2 Fab' fragments to form an F(ab')2 molecule.

An "F(ab')$_2$ fragment" contains 2 light chains and 2 heavy chains containing a portion of the constant region between the CH1 and CH2 domains, such that interchain disulfide bonds are formed between the 2 heavy chains. Thus, an F(ab')$_2$ fragment consists of 2 Fab' fragments held together by disulfide bonds between 2 heavy chains.

An "Fv region" comprises variable regions derived from both the heavy and light chains, but lacks constant regions.

The term "single chain Fv" or "scFv" antibody refers to an antibody fragment comprising the VH and VL domains of the antibody, wherein these domains are present in a single polypeptide chain. An scFv polypeptide also typically comprise a polypeptide linker between the VH and the VL domains that enables the scFv to form the desired structure for antigen-binding.

A "domain antibody" is an immunofunctional immunoglobulin fragment that contains only the variable region of the heavy chain or the light chain. In some cases, two or more VH regions are covalently linked to a peptide linker to form a bivalent domain antibody. The 2 VH regions of the bivalent domain antibody may target the same or different antigens.

A "bivalent antibody" comprises 2 antigen-binding sites. In some cases, the 2 binding sites have the same antigen specificity. However, a bivalent antibody may be bispecific.

As used herein, the term "anti-BTLA antibody" refers to an antibody raised against human BTLA or a variant thereof, or any antigen fragment thereof, unless otherwise stated.

As used herein, the term "monoclonal antibody" refers to an antibody obtained from a substantially homogeneous population of antibodies, i.e., the antibodies composing the population are identical except for possible naturally occurring mutations that may be present in minor amounts. A monoclonal antibody is highly specific and targets a single antigen epitope. In contrast, conventional (polyclonal) antibody preparations typically include a large number of antibodies targeting (or specific for) different epitopes. The modifier "monoclonal" indicates the character of an antibody obtained from a substantially homogeneous population of antibodies, and is not to be construed as producing the antibody by any particular method. For example, monoclonal antibodies used herein can be prepared by the hybridoma method or recombinant DNA method. "Monoclonal antibodies" can also be isolated using a phage antibody library.

In some embodiments, monoclonal antibodies include "chimeric" antibodies (immunoglobulins) in which a portion of the heavy and/or light chain is identical with or homologous to corresponding sequences of antibodies derived from a particular species or belonging to a particular antibody class or subclass, while the remainder of the chain is identical with or homologous to corresponding sequences of antibodies derived from another species or belonging to another antibody class or subclass, as well as fragments of such antibodies, so long as they possess the desired bioactivity.

As used herein, a "chimeric antibody" is an antibody having the variable domains of a first antibody and the constant domains of a second antibody, wherein the first and second antibodies are from different species. Typically, the variable domain is obtained from an antibody of an experimental animal such as a rodent ("parent antibody"), and the constant domain sequence is obtained from a human antibody, such that the resulting chimeric antibody is less likely to induce an adverse immune response in a human subject as compared to the parent rodent antibody.

In some embodiments, the monoclonal antibodies herein further include camelized single domain antibodies. See, e.g., Muyldermans et al. (2001) *Trends Biochem. Sci.* 26: 230; Reichmann et al. (1999) *J. Immunol.* Methods 231: 25.

As used herein, the term "diabody" refers to a small antibody fragment having two antigen-binding sites, which comprises a heavy chain variable domain (VH) linked to a light chain variable domain (VL) in one polypeptide chain (VH-VL or VL-VH). By using a linker that is too short for pairing between two domains in one chain, the domains are forced to pair with the complementary domains of the other chain to form two antigen-binding sites.

As used herein, the term "humanized antibody" refers to an antibody form containing sequences from both human and non-human (such as mouse and rat) antibodies. In general, a humanized antibody comprises substantially all of at least one, and typically two, variable domains, in which all or substantially all of the hypervariable regions correspond to those of a non-human immunoglobulin and all or substantially all of the framework regions (FRs) are those of a human immunoglobulin sequence. The humanized antibody may optionally comprise at least a portion of a human immunoglobulin constant region (Fc).

Overall, the basic antibody structural unit is known to comprise a tetramer. Each tetramer comprises two identical pairs of polypeptide chains, each pair having one "light" chain (about 25 kDa) and one "heavy" chain (about 50-70 kDa). The amino-terminal portion or fragment of each chain may comprise a variable region of about 100-110 or more amino acids primarily responsible for antigen recognition. The carboxy-terminal portion or fragment of each chain may define a constant region primarily responsible for effector function. Human light chains are generally classified as κ and λ light chains. Furthermore, human heavy chains are generally classified as μ, δ, γ, α or ε, and the antibody isotypes are defined as IgM, IgD, IgG, IgA, and IgE, respectively. Within the light and heavy chains, the variable and constant regions are connected by a "J" region of about 12 or more amino acids, and the heavy chain also comprises a "D" region of about 10 more amino acids. See generally, *Fundamental Immunology*, Chap. 7 (Paul, W. ed., 2nd edition. Raven Press, N.Y. (1989)).

The variable regions of each light/heavy chain pair are paired to form an antibody binding site. Thus, a complete IgG antibody typically has 2 binding sites. The 2 binding sites are generally identical except for those of bifunctional or bispecific antibodies.

Typically, each chain has the same general structure of relatively conserved framework regions (FRs) connected by 3 hypervariable regions (also known as complementarity determining regions or CDRs). The CDRs of 2 chains of each pair are typically aligned by the framework regions to allow binding to a particular epitope. Overall, both the light and heavy chains comprise the domains FR1, CDR1, FR2, CDR2, FR3, CDR3 and FR4 from N-terminus to C-terminus. The amino acids of each domain are generally specified according to the definitions in the following literatures: Sequences of Proteins of Immunological Interest, Kabat et al.; National Institutes of Health, Bethesda, Md.; version 5; NIH publication No. 91-3242 (1991); Kabat (1978) *Adv. Prot. Chem.* 32: 1-75; Kabat et al. (1977) *J. Biol. Chem.* 252: 6609-6616; Chothia et al. (1987) *J. Mol. Biol.* 196: 901-917; or Chothia et al. (1989) *Nature* 342: 878-883.

As used herein, the term "hypervariable region" refers to amino acid residues of an antibody responsible for antigen-binding. The hypervariable region comprises amino acid residues of a "complementarity determining region" or "CDR". As used herein, the term "framework" or "FR" residue refers to variable domain residues other than the hypervariable region residues which are defined herein as CDR residues.

An "effective amount" includes an amount sufficient to ameliorate or prevent a symptom or a sign of a medical condition. An effective amount also means an amount sufficient to allow or facilitate diagnosis. The effective amount for a particular patient or veterinary object may vary depending on factors such as the condition to be treated, the general health of the patient, the route and dose of administration and the severity of side effects. An effective amount may be the maximum dose or administration regimen that avoids significant side effects or toxic effects. The results may result in an improvement in the diagnostic measurement or parameter of at least 5%, typically at least 10%, more typically at least 20%, most typically at least 30%, preferably at least 40%, more preferably at least 50%, most preferably at least 60%, ideally at least 70%, more ideally at least 80%, and most ideally at least 90%, wherein 100% is defined as the diagnostic parameter exhibited by a normal subject (see, e.g., Maynard et al. (1996) A Handbook of SOPs for Good Clinical Practice, Interpharm Press, Boca Raton, FL; Dent (2001) Good Laboratory and Good Clinical Practice, Urch publication, London, UK).

"Homology" refers to sequence similarity between two polynucleotide sequences or between two polypeptide sequences. When a position in two compared sequences is occupied by the same base or amino acid monomer subunit, for example, if a position in each of two DNA molecules is occupied by adenine, the molecules are homologous at that position. The homology percentage between two sequences is a function of the number of matched or homologous positions shared by the two sequences/the number of the compared positions×100%. For example, two sequences are 60% homologous if 6 out of 10 positions of the two are matched or homologous when they are optimally aligned. Comparisons are typically made when aligning two sequences to acquire the maximum homology percentage.

Herein, "immune disorder" includes, such as, pathological inflammation, inflammatory disorders, and autoimmune disorders or diseases. "Immune disorder" also refers to infections, persistent infections, and proliferative conditions such as cancer, tumor, and angiogenesis, including infections, tumors, and cancers that resist eradication of the immune system. "Cancerous condition" include, such as, cancers, cancer cells, tumors, angiogenesis, and precancerous conditions such as dysplasia. The "immune lesion" and "cancerous condition" described herein are preferably both mediated by BTLA.

"Inflammatory disorder" refers to a disorder or a pathological condition in which all or a part of the pathology is caused by, for example, changes in the number, migration rate, or activation of cells of the immune system. The cells of the immune system include, such as, T cells, B cells, monocytes or macrophages, antigen-presenting cells (APCs), dendritic cells, microglia, NK cells, NKT cells, neutrophils, eosinophils, mastocytes, or any other cell of particular relevance in immunology, such as cytokine-producing endothelial or epithelial cells. The "inflammatory disorder" described herein is preferably mediated by BTLA.

An "isolated nucleic acid molecule" refers to DNA or RNA of genomic, mRNA, cDNA, or synthetic origin, or some combinations thereof, which is not associated with all or a part of a polynucleotide in which the isolated polynucleotide is naturally occurring, or is linked to a polynucleotide to which it is not naturally linked. For the purposes of the present disclosure, it should be understood that a "nucleic acid molecule" "comprising" a particular nucleotide sequence does not include an intact chromosome. In addition to the specified sequences, an isolated nucleic acid molecule "comprising" a specified nucleic acid sequence may also include a coding sequence for up to 10 or even up to 20 or more other proteins or portions or fragments thereof, or may also include an effectively linked regulatory sequence which controls the expression of the coding regions of the recited nucleic acid sequences, and/or may also include a vector sequence.

As used herein, the expressions "cell", "cell line" and "cell culture" can be used interchangeably and all such designations include their progenies. Thus, the terms "transformant" and "transformed cell" include the primary subject cell and cultures derived therefrom regardless of the number of transfers. It should also be understood that the DNA content of all progenies may not be identical due to deliberate or inadvertent mutation. Mutant progeny selected for the same function or bioactivity in the originally transformed cell are included. Although different designations are specified, it will be clear in the context.

The host cell described herein may be a prokaryotic host cell, a eukaryotic host cell or a bacteriophage. The prokaryotic host cell may be *Escherichia coli, Bacillus subtilis, Streptomyces* or *Proteus mirabilis*, etc. The eukaryotic host cell may be fungi such as *Pichia pastoris, Saccharomyces cerevisiae, Schizosaccharomyces*, and *Trichoderma*, insect cells such as *Spodoptera frugiperda*, plant cells such as tobacco, and mammalian cells such as BHK cells, CHO cells, COS cells, and myeloma cells. In some embodiments, the host cell described herein is preferably a mammalian cell, more preferably a BHK cell, a CHO cell, an NS0 cell or a COS cell.

As used herein, "polymerase chain reaction" or "PCR" generally requires that sequence information at the end of or beyond the target region must be available so that oligonucleotide primers can be designed; these primers may be identical or similar in sequence to opposite strands of the template to be amplified. The 5'-terminal nucleotide of the 2 primers may coincide with the end of the amplification material. PCR can be used to amplify specific RNA sequences, specific DNA sequences from whole genomic DNA, cDNA transcribed from total cellular RNA, phage or plasmid sequences, and the like. See generally, Mullis et al. (1987) *Cold Spring Harbor Symp. Quant. Biol.* 51: 263; Erlich ed. (1989) PCR TECHNOLOGY (Stockton Press, N.Y). As used herein, PCR is considered to be an example (but not the only one) of a nucleic acid polymerase reaction method for amplifying a nucleic acid sample, and in the method, a nucleic acid and a nucleic acid polymerase known as primers are used to amplify or generate a specific nucleic acid fragment.

Human BTLA-Specific Antibody

In general, the present invention relates to isolated antibodies or antigen-binding fragments thereof that bind to BTLA and use of such antibodies or antigen-binding fragments thereof. More specifically, the present invention provides isolated anti-BTLA antibodies or antigen-binding fragments thereof and use of these antibodies or antigen-binding fragments thereof in treating and preventing diseases. Examples of anti-BTLA antibodies include, but are not limited to, ch7, ch12, ch17, ch22, ch27, hu17, hu18, and hu19 described herein.

The present invention provides an isolated antibody or an antigen-binding fragment thereof that binds to human BTLA (B- and T-lymphocyte attenuator), comprising one or more of the following properties: A) blocking the binding of BTLA to HVEM (herpesvirus entry mediator); B) cross-reacting with cynomolgus monkey BTLA; and C) binding to human BTLA with a $K_D \leq 0.28$ nM.

In one or more embodiments, the isolated antibody or the antigen-binding fragment thereof that binds to human BTLA provided herein comprises at least one light chain CDR selected from SEQ ID NOs: 7, 8, 9, 10, 11, 12, 16, 17, 18, 22, 23, 24, 31, 32 and 33. For example, in some embodiments, the light chain CDR of the isolated antibody or the antigen-binding fragment thereof that binds to human BTLA provided herein comprises an LCDR1 that can be selected from any one of CDR sequences set forth in SEQ ID NOs: 7, 10, 16, 22 and 31; in some embodiments, the light chain CDR of the isolated antibody or the antigen-binding fragment thereof provided herein that binds to human BTLA comprises an LCDR2 that can be selected from any one of CDR sequences set forth in SEQ ID NOs: 8, 11, 17, 23 and 32; and the light chain CDR of the isolated antibody or the antigen-binding fragment thereof provided herein that binds to human BTLA comprises an LCDR3 that can be selected from any one of CDR sequences set forth in SEQ ID NOs: 9, 12, 18, 24 and 33.

In some embodiments, in the light chain CDR of the isolated antibody or the antigen-binding fragment thereof that binds to human BTLA provided herein, the LCDR1 is selected from any one of CDR sequences set forth in SEQ ID NOs: 7, 10, 16, 22 and 31, the LCDR2 is selected from any one of CDR sequences set forth in SEQ ID NOs: 8, 11, 17, 23 and 32, and the LCDR3 is selected from any one of CDR sequences set forth in SEQ ID NOs: 9, 12, 18, 24 and 33.

In some embodiments, in the isolated antibody or the antigen-binding fragment thereof that binds to human BTLA provided herein, the amino acid sequences of the LCDR1, LCDR2, and LCDR3 of the light chain CDR are selected from any one of the following groups A-E:

| Group | LCDR1 | LCDR2 | LCDR3 |
|---|---|---|---|
| A | SEQ ID NO: 7 | SEQ ID NO: 8 | SEQ ID NO: 9 |
| B | SEQ ID NO: 10 | SEQ ID NO: 11 | SEQ ID NO: 12 |
| C | SEQ ID NO: 16 | SEQ ID NO: 17 | SEQ ID NO: 18 |
| D | SEQ ID NO: 22 | SEQ ID NO: 23 | SEQ ID NO: 24 |
| E | SEQ ID NO: 31 | SEQ ID NO: 32 | SEQ ID NO: 33 |

In one or more embodiments, the isolated antibody or the antigen-binding fragment thereof that binds to human BTLA provided herein comprises at least one heavy chain CDR selected from SEQ ID NOs: 1, 2, 3, 4, 5, 6, 13, 14, 15, 19, 20, 21, 25, 26, 27, 28, 29 and 30. For example, in some embodiments, the heavy chain CDR of the isolated antibody or the antigen-binding fragment thereof that binds to human BTLA provided herein comprises an HCDR1 that can be selected from any one of CDR sequences set forth in SEQ ID NOs: 1, 4, 13, 19, 25 and 28; in some embodiments, the heavy chain CDR of the isolated antibody or the antigen-binding fragment thereof that binds to human BTLA provided herein comprises an HCDR2 that can be selected from any one of CDR sequences set forth in SEQ ID NOs: 2, 5, 14, 20, 26 and 29; and in some embodiments, the heavy chain CDR of the isolated antibody or the antigen-binding fragment thereof provided herein that binds to human BTLA comprises an LCDR3 that can be selected from any one of CDR sequences set forth in SEQ ID NOs: 3, 6, 15, 21, 27 and 30.

In some embodiments, in the heavy chain CDR of the isolated antibody or the antigen-binding fragment thereof that binds to human BTLA provided herein, the HCDR1 is selected from any one of CDR sequences set forth in SEQ ID NOs: 1, 4, 13, 19, 25 and 28; the HCDR2 is selected from any one of CDR sequences set forth in SEQ ID NOs: 2, 5, 14, 20, 26 and 29; and the LCDR3 is selected from any one of CDR sequences set forth in SEQ ID NOs: 3, 6, 15, 21, 27 and 30.

In one or more embodiments, in the isolated antibody or the antigen-binding fragment thereof that binds to human BTLA provided herein, the amino acid sequences of the HCDR1, HCDR2, and HCDR3 of the heavy chain CDR are selected from any one of the following groups F-K.

| Group | HCDR1 | HCDR2 | HCDR3 |
|---|---|---|---|
| F | SEQ ID NO: 1 | SEQ ID NO: 2 | SEQ ID NO: 3 |
| G | SEQ ID NO: 4 | SEQ ID NO: 5 | SEQ ID NO: 6 |
| H | SEQ ID NO: 13 | SEQ ID NO: 14 | SEQ ID NO: 15 |
| I | SEQ ID NO: 19 | SEQ ID NO: 20 | SEQ ID NO: 21 |
| G | SEQ ID NO: 25 | SEQ ID NO: 26 | SEQ ID NO: 27 |
| K | SEQ ID NO: 28 | SEQ ID NO: 29 | SEQ ID NO: 30 |

In one or more embodiments, in the light chain CDR of the isolated antibody or the antigen-binding fragment thereof that binds to human BTLA provided herein, the LCDR1 is selected from any one of the CDR sequences set forth in SEQ ID NOs: 7, 10, 16, 22 and 31, the LCDR2 is selected from any one of the CDR sequences set forth in SEQ ID NOs: 8, 11, 17, 23 and 32, and the LCDR3 is selected from any one of the CDR sequences set forth in SEQ ID NOs: 9, 12, 18, 24 and 33; and in the heavy chain of the isolated antibody or the antigen-binding fragment thereof that binds to human BTLA provided herein, the HCDR1 is selected from any one of the CDR sequences set forth in SEQ ID NOs: 1, 4, 13, 19, 25 and 28, the HCDR2 is selected from any one of the CDR sequences set forth in SEQ ID NOs: 2, 5, 14, 20, 26 and 29, and the HCDR3 is selected from any one of the CDR sequences set forth in SEQ ID NOs: 3, 6, 15, 21, 27 and 30.

In one or more embodiments, in the isolated antibody or the antigen-binding fragment thereof that binds to human BTLA provided herein, the amino acid sequences of the LCDR1, LCDR2, and LCDR3 of the light chain CDR are selected from any one of the following groups A-E:

| Group | LCDR1 | LCDR2 | LCDR3 |
|---|---|---|---|
| A | SEQ ID NO: 7 | SEQ ID NO: 8 | SEQ ID NO: 9 |
| B | SEQ ID NO: 10 | SEQ ID NO: 11 | SEQ ID NO: 12 |
| C | SEQ ID NO: 16 | SEQ ID NO: 17 | SEQ ID NO: 18 |
| D | SEQ ID NO: 22 | SEQ ID NO: 23 | SEQ ID NO: 24 |
| E | SEQ ID NO: 31 | SEQ ID NO: 32 | SEQ ID NO: 33 | and/or the amino acid sequences of the HCDR1, HCDR2 and HCDR3 of the heavy chain CDR are selected from any one of the following groups F-K:

| Group | HCDR1 | HCDR2 | HCDR3 |
|---|---|---|---|
| F | SEQ ID NO: 1 | SEQ ID NO: 2 | SEQ ID NO: 3 |
| G | SEQ ID NO: 4 | SEQ ID NO: 5 | SEQ ID NO: 6 |
| H | SEQ ID NO: 13 | SEQ ID NO: 14 | SEQ ID NO: 15 |
| I | SEQ ID NO: 19 | SEQ ID NO: 20 | SEQ ID NO: 21 |
| G | SEQ ID NO: 25 | SEQ ID NO: 26 | SEQ ID NO: 27 |
| K | SEQ ID NO: 28 | SEQ ID NO: 29 | SEQ ID NO: 30 |

It should be understood that each CDR sequence of the light chain, in particular each LCDR1, LCDR2, and LCDR3 sequence disclosed herein may be combined arbitrarily with each CDR sequence of the heavy chain, in particular each HCDR1, HCDR2, and HCDR3 sequence disclosed herein. For example, any one of the sequences defined herein as LCDR1 can be combined with any one of the sequences defined herein as LCDR2, any one of the sequences defined herein as LCDR3, any one of the sequences defined herein as HCDR1, any one of the sequences defined herein as HCDR2, and any one of the sequences defined herein as HCDR3 to form the entire 6 CDR domains comprised by the isolated antibody or the antigen-binding fragment thereof that binds to human BTLA described herein.

Thus, for example, in one or more embodiments, in the isolated antibody or the antigen-binding fragment thereof that binds to human BTLA provided herein, the amino acid sequences of the HCDR1, HCDR2 and HCDR3 of the heavy chain CDR and the amino acid sequences of the LCDR1, LCDR2 and LCDR3 of the light chain CDR are selected from any one of the following groups I-IX:

36, 37, 38, 39, 40, 41, 42, 43, 44, 45, 46, 47, and 48), comprise up to 0 (no change), 1, 2, 3, 4, 5, 6, 7, 8, 9, 10, 12, 15, 20 or more conservative amino acid substitutions; for example, 0-20 amino acid substitutions, or 1-15, 1-10, 1-8, or 1-5 amino acid substitutions, or substitutions totaling a number in a range consisting of any two of the above values.

Thus, the present invention also provides function-conservative variants of the antibody or the antigen-binding fragment thereof disclosed herein, i.e., variants in which one or more amino acid residues in the antibody or the antigen-binding fragment thereof disclosed herein are altered without altering the overall conformation and function of the antibody, including, but not limited to, the replacement of an

| Group | LCDR1 | LCDR2 | LCDR3 | HCDR1 | HCDR2 | HCDR3 |
| --- | --- | --- | --- | --- | --- | --- |
| I | SEQ ID NO: 7 | SEQ ID NO: 8 | SEQ ID NO: 9 | SEQ ID NO: 1 | SEQ ID NO: 2 | SEQ ID NO: 3 |
| II | SEQ ID NO: 10 | SEQ ID NO: 11 | SEQ ID NO: 12 | SEQ ID NO: 4 | SEQ ID NO: 5 | SEQ ID NO: 6 |
| III | SEQ ID NO: 16 | SEQ ID NO: 17 | SEQ ID NO: 18 | SEQ ID NO: 13 | SEQ ID NO: 14 | SEQ ID NO: 15 |
| IV | SEQ ID NO: 22 | SEQ ID NO: 23 | SEQ ID NO: 24 | SEQ ID NO: 19 | SEQ ID NO: 20 | SEQ ID NO: 21 |
| V | SEQ ID NO: 22 | SEQ ID NO: 23 | SEQ ID NO: 24 | SEQ ID NO: 25 | SEQ ID NO: 26 | SEQ ID NO: 27 |
| VI | SEQ ID NO: 31 | SEQ ID NO: 32 | SEQ ID NO: 33 | SEQ ID NO: 28 | SEQ ID NO: 29 | SEQ ID NO: 30 |
| VII | SEQ ID NO: 7 | SEQ ID NO: 8 | SEQ ID NO: 9 | SEQ ID NO: 4 | SEQ ID NO: 5 | SEQ ID NO: 6 |
| VIII | SEQ ID NO: 10 | SEQ ID NO: 11 | SEQ ID NO: 12 | SEQ ID NO: 1 | SEQ ID NO: 2 | SEQ ID NO: 3 |
| IX | SEQ ID NO: 10 | SEQ ID NO: 11 | SEQ ID NO: 12 | SEQ ID NO: 13 | SEQ ID NO: 14 | SEQ ID NO: 15 |

In one or more embodiments, the isolated antibody or the antigen-binding fragment thereof that binds to human BTLA provided herein comprises a light chain variable region and a heavy chain variable region, wherein the amino acid sequence of the light chain variable region is selected from SEQ ID NOs: 36, 37, 39, 41, 44, 46, 47 and 48; and/or the amino acid sequence of the heavy chain variable region is selected from SEQ ID NOs: 34, 35, 38, 40, 42, 43 and 45.

In one or more embodiments, the isolated antibody disclosed herein comprises a heavy chain constant region, preferably a human constant region, e.g., a γ1, γ2, γ3, or γ4 human heavy chain constant region or a variant thereof. In another embodiment, the isolated antibody disclosed herein comprises a light chain constant region, preferably a human light chain constant region, e.g., a κ or κ human light chain region or a variant thereof. By way of example and not limitation, the human heavy chain constant region may be γ4 and the human light chain constant region may be κ. In one embodiment, the Fc region of the antibody may be γ4 with conservative modifications or conservative substitutions or conservative mutations.

Herein, the term "conservatively modified variant" or "conservative substitution" or "conservative mutation" refers to the substitution of an amino acid in a protein by another amino acid having similar properties (e.g., charge, side chain size, hydrophobicity/hydrophilicity, backbone conformation, and rigidity) such that changes may be made frequently without altering the bioactivity of the protein. Those skilled in the art recognize that single amino acid substitution in the non-essential region of a polypeptide will generally not significantly alter bioactivity (see, e.g., Watson et al., (1987) Molecular Biology of the Gene, The Benjamin/Cummings Pub. Co., page 224 (4th edition)). In addition, substitutions of structurally or functionally similar amino acids are unlikely to destroy bioactivity. The antibodies or the antigen-binding fragments thereof of various embodiments of the present invention comprise polypeptide chains having the sequences which, when compared to a particular amino acid sequence disclosed herein (e.g., SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, amino acid with an amino acid having similar properties. In general, the number of replacements may be in the ranges described above, such as 0-20 conservative amino acid substitutions.

In one or more embodiments, the isolated antibody or the antigen-binding fragment thereof that binds to human BTLA disclosed herein is a single chain Fv antibody; in some embodiments, the antibody or the antigen-binding fragment thereof is a Fab antibody; in some embodiments, the antibody or the antigen-binding fragment thereof is an Fab' antibody; and in some embodiments, the antibody or the antigen-binding fragment thereof is an (Fab')$_2$ antibody.

In one or more embodiments, the light chain variable region of the isolated antibody or the antigen-binding fragment thereof that binds to human BTLA disclosed herein comprises an amino acid sequence set forth in SEQ ID NO: 36, and the heavy chain variable region comprises an amino acid sequence set forth in SEQ ID NO: 34 or 35.

In one or more embodiments, the light chain variable region of the isolated antibody or the antigen-binding fragment thereof that binds to human BTLA disclosed herein comprises an amino acid sequence set forth in SEQ ID NO: 37, and the heavy chain variable region comprises an amino acid sequence set forth in SEQ ID NO: 34 or 35.

In one or more embodiments, the light chain variable region of the isolated antibody or the antigen-binding fragment thereof that binds to human BTLA disclosed herein comprises an amino acid sequence set forth in SEQ ID NO: 39, and the heavy chain variable region comprises an amino acid sequence set forth in SEQ ID NO: 38.

In one or more embodiments, the light chain variable region of the isolated antibody or the antigen-binding fragment thereof that binds to human BTLA disclosed herein comprises an amino acid sequence set forth in SEQ ID NO: 41, and the heavy chain variable region comprises an amino acid sequence set forth in SEQ ID NO: 40 or 42.

In one or more embodiments, the light chain variable region of the isolated antibody or the antigen-binding fragment thereof that binds to human BTLA disclosed herein comprises an amino acid sequence set forth in SEQ ID NO:

44, and the heavy chain variable region comprises an amino acid sequence set forth in SEQ ID NO: 43.

In one or more embodiments, the light chain variable region of the isolated antibody or the antigen-binding fragment thereof that binds to human BTLA disclosed herein comprises an amino acid sequence set forth in SEQ ID NO: 46, 47 or 48, and the heavy chain variable region comprises an amino acid set forth in SEQ ID NO: 45.

The present invention also provides an isolated nucleic acid, e.g., DNA, encoding an isolated antibody or an antigen-binding fragment thereof disclosed herein. In some embodiments, the isolated nucleic acid disclosed herein encodes an antibody or an antigen-binding fragment thereof comprising at least one mature antibody light chain variable (VL) domain and at least one mature antibody heavy chain variable (VH) domain, wherein the VL domain comprises at least 3 CDRs having sequences selected from SEQ ID NOs: 7-8, 10-12, 16-18, 22-24 and 31-33, and the VH domain comprises at least 3 CDRs having sequences selected from SEQ ID NOs: 1-3, 4-6, 13-15, 19-21, 25-27 and 28-30. In one embodiment, the isolated nucleic acid encodes mature light and heavy chain variable region sequences set forth in SEQ ID NO: 36 and SEQ ID NO: 34, respectively. In one embodiment, the isolated nucleic acid encodes mature light and heavy chain variable region sequences set forth in SEQ ID NO: 36 and SEQ ID NO: 35, respectively. In one embodiment, the isolated nucleic acid encodes mature light and heavy chain variable region sequences set forth in SEQ ID NO: 37 and SEQ ID NO: 34, respectively. In one embodiment, the isolated nucleic acid encodes mature light and heavy chain variable region sequences set forth in SEQ ID NO: 37 and SEQ ID NO: 35, respectively. In one embodiment, the isolated nucleic acid encodes mature light and heavy chain variable region sequences set forth in SEQ ID NO: 39 and SEQ ID NO: 38, respectively. In one embodiment, the isolated nucleic acid encodes mature light and heavy chain variable region sequences set forth in SEQ ID NO: 41 and SEQ ID NO: 40, respectively. In one embodiment, the isolated nucleic acid encodes mature light and heavy chain variable region sequences set forth in SEQ ID NO: 41 and SEQ ID NO: 42, respectively. In one embodiment, the isolated nucleic acid encodes mature light and heavy chain variable region sequences set forth in SEQ ID NO: 44 and SEQ ID NO: 43, respectively. In one embodiment, the isolated nucleic acid encodes mature light and heavy chain variable region sequences set forth in SEQ ID NO: 46 and SEQ ID NO: 45, respectively. In one embodiment, the isolated nucleic acid encodes mature light and heavy chain variable region sequences set forth in SEQ ID NO: 47 and SEQ ID NO: 45, respectively. In one embodiment, the isolated nucleic acid encodes mature light and heavy chain variable region sequences set forth in SEQ ID NO: 48 and SEQ ID NO: 45, respectively. In one or more embodiments, the isolated nucleic acid encodes both a light chain and a heavy chain on a single nucleic acid molecule, while in other embodiments, the isolated nucleic acid encodes a light chain and a heavy chain on two or more independent nucleic acid molecules.

The present invention also provides an expression vector comprising the isolated nucleic acid disclosed herein. The present invention also provides a host cell comprising the expression vector disclosed herein. The present invention also relates to a method for producing the antibody or the antigen-binding fragment thereof disclosed herein.

The present invention also relates to an antibody or an antigen-binding fragment thereof that binds to the same epitope on human BTLA as antibodies ch7, ch12, ch17, ch22, ch27, hu17, hu18, and hu19 described herein, e.g., an antibody that is capable of cross-blocking the binding of any of the antibodies disclosed herein.

Disease and Treatment or Prevention Thereof

The present invention also provides a method for treating or preventing a subject (including a human subject) in need of the treatment with an isolated antibody or an antigen-binding fragment thereof using an antibody or an antigen-binding fragment thereof (preferably a humanized antibody) disclosed herein. The method generally comprise administering to a subject in need a therapeutically or prophylactically effective amount of an antibody or an antigen-binding fragment thereof, or a pharmaceutical composition comprising the antibody or the antigen-binding fragment thereof according to any one of the embodiments of the present invention. Suitable routes of administration may be selected as appropriate, including but not limited to oral, intravenous, subcutaneous, intramuscular, intra-arterial, intra-articular (e.g., in arthritic joints), by inhalation, aerosol delivery, intratumoral administration, and the like.

The subject typically suffers from BTLA-mediated diseases, i.e., diseases that benefit from elimination, inhibition, or reduction of BTLA activity. Generally, BTLA-mediated diseases are all diseases associated with immunosuppression, including autoimmune diseases, transplant rejection, tumors, and the like. The tumors include melanoma, breast cancer, renal cancer, prostate cancer, colon cancer, lung cancer, pancreatic cancer, bone cancer, skin cancer, head or neck cancer, uterine cancer, ovarian cancer, rectal cancer, anal cancer, stomach cancer, testicular cancer, esophageal cancer, small intestine cancer, cervical cancer, vaginal cancer, Hodgkin's disease, non-Hodgkin's lymphoma, esophageal cancer, cancer of the endocrine system, thyroid cancer, carcinoma of adrenal gland, soft tissue cancer, urethral cancer, chronic or acute leukemia, chronic myeloid leukemia, acute lymphoblastic leukemia, chronic lymphocytic leukemia, childhood solid tumor, lymphocytic lymphoma, bladder cancer, kidney or ureteral cancer, renal pelvis cancer, neoplasms of the central nervous system, primary central nervous system lymphoma, tumor angiogenesis, spinal axis tumor, brain stem glioma, pituitary adenoma, Kaposi's sarcoma, epidermoid carcinoma, squamous cell carcinoma, T-cell lymphoma, environmentally induced cancers including those induced by asbestos, and combinations of the cancers. The autoimmune diseases include organ-specific autoimmune diseases and systemic autoimmune diseases; the organ-specific autoimmune diseases include chronic lymphocytic thyroiditis, hyperthyroidism, insulin-dependent diabetes mellitus, myasthenia gravis, ulcerative colitis, pernicious anemia with chronic atrophic gastritis, goodpasture's syndrome, pemphigus vulgaris, pemphigoid, primary biliary cirrhosis, multiple sclerosis, acute idiopathic polyneuritis, and the like; and the systemic autoimmune diseases include systemic lupus erythematosus, rheumatoid arthritis, systemic vasculitis, scleroderma, pemphigus, dermatomyositis, mixed connective tissue disease, autoimmune hemolytic anemia, ulcerative colitis, and the like.

Such treatments may also include the administration of one or more other therapeutic agents, such as tumor vaccines, standard tumor chemotherapy therapeutic agents, and other immune inducers.

Kit

The present invention also provides a kit comprising components of a combination drug disclosed herein. The kit disclosed herein comprises one or more components, including but not limited to an antibody or an antigen-binding fragment that specifically binds to BTLA described herein (e.g., antibodies ch7, ch12, ch17, ch22, ch27, hu17, hu18, and hu19, but not limited to those described above) and one or more other components, including but not limited to a pharmaceutically acceptable carrier and/or a chemotherapeutic agent described herein. The antibodies or the antigen-binding fragments and/or chemotherapeutic agents may be formulated in pure compositions or combined with a pharmaceutically acceptable carrier in pharmaceutical compositions.

In one embodiment, a kit comprises an antibody or an antigen-binding fragment thereof disclosed herein (e.g., antibodies ch7, ch12, ch17, ch22, ch27, hu17, hu18, and hu19, but not limited to those described above) or a pharmaceutical composition thereof included in one container (e.g., a sterile glass or plastic vial) one container (e.g., a sterile glass or plastic vial), and an antibody or an antigen-binding fragment thereof or a pharmaceutical composition thereof disclosed herein, and/or a chemotherapeutic drug included in another container (e.g., a sterile glass or plastic vial).

In another embodiment of the present invention, a kit comprises a combination drug disclosed herein, comprising an antibody or an antigen-binding fragment (e.g., antibodies ch7, ch12, ch17, ch22, ch27, hu17, hu18 and hu19, but not limited to those described above) in a single common container, together with a pharmaceutically acceptable carrier, optionally in combination with one or more components of a chemotherapeutic agent formulated together, optionally in a pharmaceutical composition.

A kit may comprise a package insert that provides information about the pharmaceutical composition and dosage form in the kit. Such information generally helps patients and physicians to use the attached pharmaceutical composition and dosage form effectively and safely. For example, the following information may be provided in the package insert regarding the combination drug disclosed herein: pharmacokinetics, pharmacodynamics, clinical studies, efficacy parameters, indications and usage, contraindications, warnings, precautions, adverse reactions, overuse, proper dosage and administration, supply specifications, proper storage conditions, references, manufacturer/wholesaler information, and patent information.

Pharmaceutical Composition and Administration

The present invention also provides a pharmaceutical composition comprising any one of the anti-human BTLA antibodies or the antigen-binding fragments thereof described herein. As used herein, the term "pharmaceutical composition" refers to a combination of at least one drug and optionally a pharmaceutically acceptable carrier or an excipient combined together to achieve a certain objective. In some embodiments, the pharmaceutical composition includes temporally and/or spatially separated combinations, so long as they can act together to achieve the objective of the present invention. For example, the components comprised in the pharmaceutical composition (e.g., the antibody, the nucleic acid molecule, the combination of nucleic acid molecules and/or the conjugate according to the present invention) may be administered to a subject as a whole or separately. When administered to a subject separately, the components comprised in the pharmaceutical composition may be administered to the subject simultaneously or sequentially. Preferably, the pharmaceutically acceptable carrier is water, aqueous buffer solutions, isotonic salt solutions such as PBS (phosphate buffer saline), glucose, mannitol, dextrose, lactose, starch, magnesium stearate, cellulose, magnesium carbonate, 0.3% glycerol, hyaluronic acid, ethanol, or polyalkylene glycols such as polypropylene glycol, triglyceride, and the like. The type of the pharmaceutically acceptable carrier used depends particularly on the composition according to the present invention is formulated for oral nasal, intradermal, subcutaneous, intramuscular or intravenous administration. The composition according to the present invention may comprise wetting agents, emulsifying agents or buffer substances as additives. The immunoconjugate disclosed herein may comprise an antibody or an antigen-binding fragment thereof according to any one of the embodiments herein conjugated with a therapeutic agent, preferably an immunotoxin, a radioisotope, a medicament or a cytotoxic agent known in the art and commonly used in the preparation of immunoconjugates.

To prepare a pharmaceutical or sterile composition of the anti-human BTLA antibody or the antigen-binding fragment thereof disclosed herein, the antibody or the antigen-binding fragment thereof can be mixed with a pharmaceutically acceptable carrier or an excipient. See, e.g., Remington's Pharmaceutical Sciences and U.S. Pharmacopeia: National Formulary, Mack Publishing Company, Easton, PA (1984).

The pharmaceutical composition disclosed herein may be prepared in a variety of suitable dosage forms known in the art, including but not limited to lyophilized powder, ointment, aqueous solution or suspension, and the like. Dosage forms such as lyophilized powder, ointment, aqueous solution or suspension of the therapeutic agent and diagnostic agent can be prepared by mixing with an acceptable carrier, an excipient or a stabilizer (see, e.g., Hardman et al. (2001) Goodman and Gilman's The Pharmaceutical Basis of Therapeutics, McGraw-Hill, New York, NY; Gennaro (2000) Remington: The *Science* and Practice of Pharmacy, Lippincott, Williams, and Wilkins, New York, NY; Avis et al. (eds.) (1993) Pharmaceutical Dosage Forms: Parenteral Medications, Marcel Dekker, NY; Lieberman et al. (eds.) (1990) Pharmaceutical Dosage Forms: Tablets, Marcel Dekker, NY; Lieberman et al. (eds.) (1990) Pharmaceutical Dosage Forms: Disperse Systems, Marcel Dekker, NY; Weiner and Kotkoskie (2000) Excipient Toxicity and Safety, Marcel Dekker, Inc., New York, NY).

The dosage regimen depends on several factors including the serum or tissue turnover rate of the therapeutic antibody, the level of symptoms, the immunogenicity of the therapeutic antibody, and the accessibility of the target cells in the biological matrix. Preferably, the dosage regimen delivers sufficient therapeutic antibody to achieve an improvement in the target disease state while minimizing adverse side effects. Thus, the amount of biologics delivered depends in part on the particular therapeutic antibody and the severity of the condition to be treated. Guidance in selecting appropriate doses of therapeutic antibody is available (see, e.g., Wawrzynczak (1996) Antibody Therapy, Bios Scientific Pub. Ltd, Oxfordshire, UK; Kresina (ed.) (1991) Monoclonal Antibodies, Cytokines and Arthritis, Marcel Dekker, New York, NY; Bach (ed.) (1993) Monoclonal Antibodies and Peptide Therapy in Autoimmune Diseases, Marcel Dekker, New York, NY; Baert et al. (2003) *New Engl. J. Med.* 348: 601-608; Milgrom et al. (1999) *New Engl. J. Med.* 341: 1966-1973; Slamon et al. (2001) *New Engl. J. Med.* 344: 783-792; Beniaminovitz et al. (2000) *New Engl. J Med.* 342: 613-619; Ghosh et al. (2003) *New Engl. J. Med.* 348: 24-32; Lipsky et al. (2000) *New Engl. J. Med.* 343: 1594-1602).

Use

The present invention provides use of the anti-BTLA antibody and the antigen-binding fragment thereof according to any one of the embodiments herein in treating, preventing and diagnosing BTLA-mediated diseases. In some embodiments, the present invention provides the anti-BTLA antibody and the antigen-binding fragment thereof according to any one of the embodiments herein for use in the treatment, prevention, and diagnosis of BTLA-mediated diseases.

EXAMPLES

The following examples are provided to demonstrate and further illustrate some preferred embodiments and aspects of the present invention and should not be construed as limiting the scope of the present invention.

Example 1. Cloning of Extracellular Domain of Human BTLA into Eukaryotic Expression Plasmid Plasmid HG11895-G-N containing cDNA sequences of human BTLA gene was purchased from Sino Biological, and human BTLA extracellular fragment (nucleotide sequence set forth in SEQ ID NO: 49) was PCR-amplified using a forward primer 5'-gtacGCTCTTCATGTaaagaat-catgtgatgtacagcttta-3' (SEQ ID NO: 50) and a reverse primer 5'-gatcGCTCTTCTAGCatacaggagccagggtctgcttgcca-3' (SEQ ID NO: 51). After digested by BSPQI, the amplified fragments were inserted into a self-constructed eukaryotic expression plasmid system (HX1-FC) to generate an expression plasmid of human BTLA extracellular domain protein (hBTLA-ECD-FC). 293E cells were transfected with this plasmid by PEI, and after 6 days, the culture supernatant was collected and the recombinant protein of human BTLA extracellular domain (hBTLA-ECD-FC) was purified by affinity chromatography.

FIG. 1 shows the SDS-PAGE electropherogram of the human BTLA extracellular domain protein.

Figure 2:
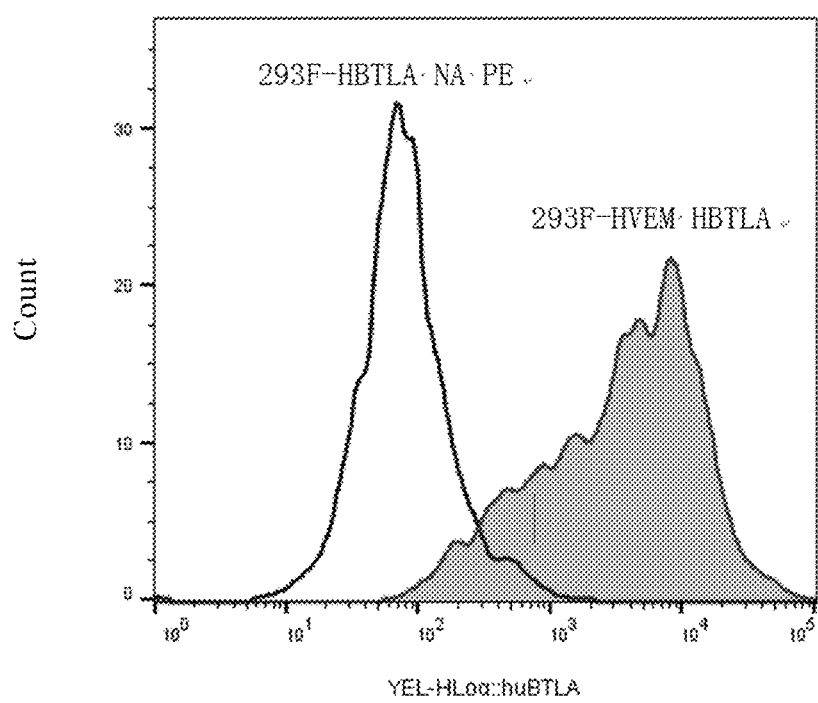
FIG. 2 shows the binding capacity of BTLA to HVEM assayed by a flow cytometer.

Example 2. Assay on the Binding of Recombinant Protein hBTLA-ECD-FC to Human HVEM on Cells by FACS A 293F stable cell line (hHVEM-293F) expressing human HVEM (Gene Bank: NP_003811.2) was constructed. The hHVEM-293F cell suspension was mixed with biotin-labeled hBTLA (300 ng/mL) and incubated at room temperature for 30 minutes. After washing the cells 3 times with an FACS buffer, 5 µg/mL NA-PE was added and the mixture was incubated for 30 minutes. After washing the cells 3 times with an FACS buffer, the binding of BTLA recombinant protein to HVEM on the surface of 293F cells was assayed and verified by a flow cytometer. The results are shown in FIG. 2.

Example 3. Preparation of Anti-BTLA Murine Antibody 3.1. Immunization of Animals
The recombinant protein hBTLA-ECD-FC obtained in Example 1 was used as an antigen and mixed with an equal amount of immunoadjuvant (Freund's adjuvant), and 5 female Balb/c mice aged 6 weeks were subjected to subcutaneous immunization. A booster immunization was performed every two weeks after the primary immunization, totaling 6 times of immunization.
3.2. Cell Fusion
After the final booster injection, the inguinal lymph nodes of the mice were taken and ground in normal saline, and the lymphocyte-rich suspension was taken and fused with SP2/0 cells according to a conventional electroporation method (see the handbook of the BTX electroporation instrument). The fused cells were cultured in a DMEM complete medium (Corning) containing HAT at 8% $CO_2$, 37° C.

Example 4. Screening Experiments on Hybridoma Cells

In 11,500 different polyclonal hybridoma cell lines, 560 clones secreting antibodies that bind to human BTLA protein were selected by enzyme-linked immunosorbent assay (ELISA). Of the 560 clones, 33 clones were able to bind to BTLA expressed on 293F cells; and of these 33 clones, 16 clones had the ability to inhibit the binding of biotin-labeled human BTLA to HVEM on 293F. The first 4 of these 16 clones (2D12, 3B3, 3E3 and 6A7) were mainly involved in subsequent experiments, and the specific screening experiments were as follows.
4.1. Assay on the Binding of Hybridoma Antibodies to hBTLA by ELISA
Hybridoma cell lines secreting antibodies that bind to hBTLA were screened by ELISA. A 384-well microplate was coated with 1 µg/mL hBTLA, and incubated overnight at 4° C. The solution in wells was then discarded, and the wells were washed 3 times with washing buffer, and blocked for 60 minutes with PBS containing 1% BSA. After being washed 3 times with washing buffer, the wells were added with the hybridoma culture supernatant, incubated at room temperature for 60 minutes, and washed 3 times with the washing buffer. Then, HRP-labeled goat anti-mouse IgG secondary antibody diluted at 1:5000 was added and the mixture was incubated at room temperature for 30 minutes. After washing the wells three times with washing buffer, 30 µL of TMB substrate solution was added for color development at room temperature for 10 minutes, and then the reaction was stopped with 30 µL of hydrochloric acid solution (2M) and the absorbance was read at 450 nm.
4.2. Assay on Species Specificity of the Binding of Hybridoma Antibodies to hBTLA by ELISA
Hybridoma cell lines secreting antibodies that bind to cynomolgus monkey BTLA were screened by ELISA. A 96-well microplate was coated with 1 µg/mL cynomolgus BTLA and incubated at room temperature for 60 minutes. The solution in wells was then discarded, and the wells were washed 3 times with washing buffer, and blocked for 60 minutes with PBS containing 1% BSA. After being washed 3 times with washing buffer, the wells were added with the hybridoma culture supernatant, incubated at room temperature for 60 minutes, and washed 3 times with the washing buffer. Then, HRP-labeled goat anti-mouse IgG secondary antibody diluted at 1:5000 was added and the mixture was incubated at room temperature for 30 minutes. After washing the wells three times with washing buffer, 100 µL of TMB substrate solution was added for color development at room temperature for 10 minutes, and then the reaction was stopped with 100 µL of hydrochloric acid solution (2M) and the absorbance was read at 450 nm.
4.3. Assay on Hybridoma Antibodies' Blocking of the Binding of BTLA to HVEM by FACS
The culture supernatant of the 33 antibodies was mixed with biotin-labeled human BTLA (300 ng/mL) and incubated at room temperature for 30 minutes. The mixture was then incubated with a suspension of hHVEM-293F stable cell line for 30 minutes at room temperature. After washing the cells 3 times with an FACS buffer, 5 µg/mL NA-PE was added and the mixture was incubated for 30 minutes. After washing the cells 3 times with an FACS buffer, the blocking of the binding of human BTLA to HVEM on the surface of 293F cells by antibodies secreted by the hybridoma cells was assayed and verified by a flow cytometer.

Example 5. Acquisition of Variable Region Sequences of Candidate Antibodies (Represented by Kabat or IMGT)

The DNA sequences of the variable regions of the mouse antibodies expressed by the candidate hybridomas were determined using a degenerate primer-based PCR method. Briefly, hybridoma cell lines were separately expanded, cells were harvested by centrifugation at 1000 rpm, and total RNA was extracted with Trizol. After first strand cDNA was synthesized using the total RNA as a template, the DNA sequence of a corresponding variable region was PCR-amplified using the first strand cDNA as a subsequent template, and PCR primers used are based on an Ig-primer group. After isolating and purifying PCR products, and sequencing the amplified products, the sequences of the heavy chain variable region and light chain variable region of the candidate hybridoma were obtained.

The NCBI Ig-Blast (ncbi.nlm.nih.gov/projects/igblast/) was used to search for consensus sequences in germline and rearranged Ig variable region sequence databases. Complementarity determining regions (CDRs) were identified by sequence annotation and by Internet-based sequence analysis (Imgt.org/IMGT_vquest/share/textes/index.html and ncbi.nlm.nih.gov/igblast/) based on Kabat (Wu, T. T and Kabat, E. A. 1970 *J. Exp. Med.*, 132: 211-250) and IMGT system (Lefranc M.-P. et al., 1999 *Nucleic Acids Research*, 27, 209-212).

The amino acid sequences of the light and heavy chain variable regions and CDRs encoded in the hybridoma cells are shown below (where the CDRs expressed in bold and underlined are demarcated based on the Kabat system, and the CDRs expressed in italics and bold are demarcated based on the IMGT system):

2D12 HC1
EVQLQQSGAELVKPGASVNLSCTASGFAIRDTYLHWVKQRPEQVLEWTG
RIDPANGNTKYDPRFQGKATLTADTSSNTA*YLHLS*SLTSEDTAVYYCVA
DYYGSSLFDYWGQGTTLTVSS (SEQ ID NO: 34, sequences
of 3 HCDRs correspond to SEQ ID NOs: 1-3,
respectively)

2D12 HC2
EVQLQQSGAELVKPGASVKLSCTVSGFNIKDSYIHWVKQRPEQGLEWIG
RIDPANGNTKYDPKFRGKATITADASSNTAA*LQVS*SLTSEDTAVYFCVG
DHYGSSLFDYWGHGTTLTVSS (SEQ ID NO: 35, sequences
of 3 HCDRs correspond to SEQ ID NOs: 4-6,
respectively)

2D12 LC1
DVVMTQTPLTLSVTIGQPASISCKSSQSLLDSDGKTYLNWLLQRPGQSP
KRLIYVLSKLESGVPDRFTGVGSGTDFTLKISRVEAVDLGVYYC**WQGTH
FPYT**FGGGTKLEIK (SEQ ID NO: 36, sequences of 3
LCDRs correspond to SEQ ID NOs: 7-9, respectively)

2D12 LC2
EVVMTQTPLTLSVTIGQSASISCKSSQSLLDSDGKTYLNWFLQRPGQSP
KRLMHLVSKLDSGVPDRFTGSGSGTDFTLKISGVEAEDLGVYYC**WQGTY
FPYT**FGGGTKLETK (SEQ ID NO: 37, sequences of 3
LCDRs correspond to SEQ ID NOs: 10-12,
respectively)

3B3 HC
EVQLQQSGADLVKPGASVKLSCTASGFNFKHTYAHWVKQRPEQGLEWIG
RIDPANGNTKYDPKFQGKATMTADTASNAAFLQLSSLTSEDTAVYYCVA
DHYGSSLLDYWGQGTSLTVSS (SEQ ID NO: 38, sequences
of 3 HCDRs correspond to SEQ ID NOs: 13-15,
respectively)

3B3 LC
DIQMTQSPSSLSASLGGKVTITCKASQDINKYIAWYQHKPGKGPRLLIH
YTSTLQPGIPSRFSGSGSGSDYSLTISSLESEDSANYYC**LQYATYAPPA
VSIF**GAGTKLELK (SEQ ID NO: 39, sequences of 3
LCDRs correspond to SEQ ID NOs: 16-18,
respectively)

3E3 HC1
EVQLQQSGADLVKPGASVKLSCTASGFNIKDTYVHWVKQRPEQGLEWIG
RIDPANGHTKFDPKFQGKATITADTSSNTANLQISSLTSEDTAVYYCVS
DYYGSSLLDYWGQGTTLTVSS (SEQ ID NO: 40, sequences
of 3 HCDRs correspond to SEQ ID NOs: 19-21,
respectively)

3E3 LC
DPDSTHFVDYHWTTCLHLLQVQ*SEPPSEDGKTY*LSWIFQMFHLSPKRLI
Y*VVS*KLNSGVPVRLSANHSRTDFTLKISRVEAEDLGVYYC*WQGTHFPYT*
FGGGTKLEIK (SEQ ID NO: 41, sequences of 3 LCDRs
correspond to SEQ ID NOs: 22-24, respectively)

3E3 HC2
EVQLQQSGAELVRPGASVKLSCTVSGFNIKDTYVHWVKQRPEQGLEWIG
RIDPANGHTKYDPKLQGTATITADTSSNTAYLQLSSLTSEDTAVYYCAT
DYYGSSLLDYWGQGTTLTVSS (SEQ ID NO: 42, sequences
of 3 HCDRs correspond to SEQ ID NOs: 25-27,
respectively)

6A7 HC
EVHLQQSGTELMKPGASVKLSCTASGLNIRDTYMHWVKQRPEQGLEWIG
RIDPANGNTKFDPKFQGKATLTSDTSSNTAYLHFSSLTSEDAAVYYCVS
DHYGSSLLDYWGQGTSLTVSS (SEQ ID NO: 43, sequences
of 3 HCDRs correspond to SEQ ID NOs: 28-30,
respectively)

6A7 LC
DIKMTQSPSSMYASLGERVTITCKASQDIKSYLSWYQQKPWKSPKTLIY
YATSLADGVPSRFSGSGSGQDYSLTITSLESDDTATYYC**LQHGADAAPT
VSIF**GGGTKLEIK (SEQ ID NO: 44, sequences of 3
LCDRs correspond to SEQ ID NOs: 31-33,
respectively)

Example 6. Construction of Chimeric Antibody Expression Vectors

The heavy chain variable region and light chain variable region genes of the candidate murine antibody were fused to the N-terminus of the FC and κ chain constant regions of human IgG4, respectively, by standard PCR techniques, and inserted into pcDNA3.1 vectors to construct expression plasmids of chimeric heavy or light chains. The expression cells were transfected by pairwise combination of the above expression vector plasmids of the heavy chain and the light chain, followed by purification and extraction to acquire the chimeric antibodies ch7, ch12, ch17, ch22 and ch27. The amino acid sequences of the light and heavy chain variable regions and CDRs encoded in the hybridoma cells are shown below

| Chimeric antibody No. | Chain/CDR | Sequence No. |
|---|---|---|
| | Heavy chain | |
| ch7 | HCDR1 | SEQ ID NO: 4 |
| | HCDR2 | SEQ ID NO: 5 |
| | HCDR3 | SEQ ID NO: 6 |
| | Light chain | |
| | LCDR1 | SEQ ID NO: 10 |
| | LCDR2 | SEQ ID NO: 11 |
| | LCDR3 | SEQ ID NO: 12 |

-continued

| Chimeric antibody No. | Chain/CDR | Sequence No. |
|---|---|---|
| | Heavy chain | |
| ch12 | HCDR1 | SEQ ID NO: 13 |
| | HCDR2 | SEQ ID NO: 14 |
| | HCDR3 | SEQ ID NO: 15 |
| | Light chain | |
| | LCDR1 | SEQ ID NO: 10 |
| | LCDR2 | SEQ ID NO: 11 |
| | LCDR3 | SEQ ID NO: 12 |
| | Heavy chain | |
| ch17 | HCDR1 | SEQ ID NO: 19 |
| | HCDR2 | SEQ ID NO: 20 |
| | HCDR3 | SEQ ID NO: 21 |
| | Light chain | |
| | LCDR1 | SEQ ID NO: 10 |
| | LCDR2 | SEQ ID NO: 11 |
| | LCDR3 | SEQ ID NO: 12 |
| | Heavy chain | |
| ch22 | HCDR1 | SEQ ID NO: 25 |
| | HCDR2 | SEQ ID NO: 26 |
| | HCDR3 | SEQ ID NO: 27 |
| | Light chain | |
| | LCDR1 | SEQ ID NO: 10 |
| | LCDR2 | SEQ ID NO: 11 |
| | LCDR3 | SEQ ID NO: 12 |
| | Heavy chain | |
| ch27 | HCDR1 | SEQ ID NO: 28 |
| | HCDR2 | SEQ ID NO: 29 |
| | HCDR3 | SEQ ID NO: 30 |
| | Light chain | |
| | LCDR1 | SEQ ID NO: 10 |
| | LCDR2 | SEQ ID NO: 11 |
| | LCDR3 | SEQ ID NO: 12 |

Example 7. Assay on the Binding of Chimeric Antibodies to hBTLA by ELISA

The binding ability of the chimeric antibodies to hBTLA was assayed by ELISA. A 96-well microplate was coated with 0.5 µg/mL hBTLA and incubated at 37° C. for 60 minutes. The solution in wells was then discarded, and the wells were washed 3 times with washing buffer, and blocked for 60 minutes with PBS containing 2% BSA. After being washed 3 times with washing buffer, the wells were added with gradiently-diluted antibodies, incubated at 37° C. for 60 minutes, and washed 3 times with washing buffer before adding a HRP-labeled mouse anti-human IgG4 secondary antibody diluted at 1:10000. The mixture was incubated at 37° C. for 1 hour, washed three times with washing buffer, and added with 100 µL of TMB substrate solution for color development at room temperature for 30 minutes, then the reaction was stopped with 100 µL of 2M hydrochloric acid solution and the absorbance was read at 450 nm.

Figure 3:
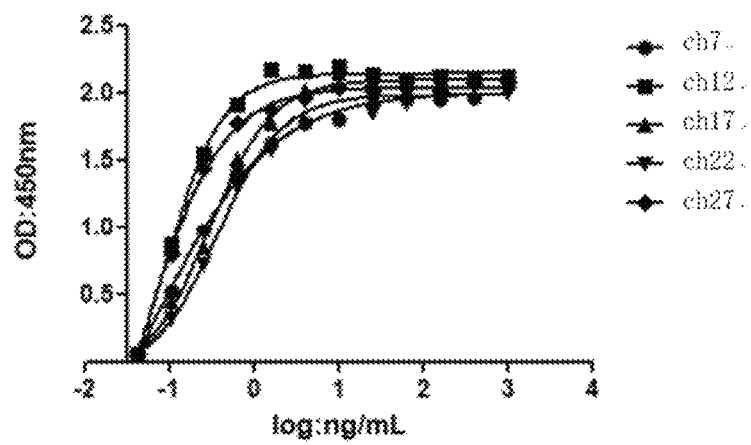
FIG. 3 shows an ELISA assay on the binding of chimeric antibodies to human BTLA.

The results are shown in FIG. 3. The chimeric antibodies ch7, ch12, ch17, ch22 and ch27 can specifically bind to hBTLA. The $EC_{50}$ values are shown in Table 1 below.

TABLE 1

Data on specific binding of chimeric antibodies to human BTLA

| Chimeric antibody | ch7 | ch12 | ch17 | ch22 | ch27 |
|---|---|---|---|---|---|
| $EC_{50}$ (ng/ml) | 0.066 | 0.094 | 0.298 | 0.373 | 0.052 |

Example 8. Assay on Chimeric Antibodies' Blocking of the Binding of BTLA to HVEM by FACS The ability of the chimeric antibodies to block the binding of hBTLA to hHVEM expressed on 293F cells was assayed by FACS. hHVEM-293F stable cells were centrifuged and resuspended in an FACS buffer after digestion, and then added into a 96-well round-bottom plate at a density of $2.5 \times 10^4$ cells/50 µL. Then the cells were mixed with previously biotin-labeled hBTLA (1 µg/mL) protein, incubated at 4° C. for 15 minutes, followed by mixing with 50 µL of chimeric antibody diluent (initial concentration: 5 µg/mL, 3-fold titration) at different concentrations, and incubating at room temperature for 30 minutes. After being washed with an FACS buffer twice, the cells were added with 100 µL of goat anti-human IgG-PE antibody, incubated for 30 minutes away from light, and assayed by FACS after two washes with an FACS buffer. The washed cells were resuspended in 4° C. buffer containing propidium iodide (PI) and 0.02% sodium azide that prevents receptor internalization and analyzed by flow cytometry. Viable cells were gated on the basis of PI positive cells being excluded from the FSC/SSC gate and their geometric mean fluorescence intensity (MFI) was measured. The data were analyzed using a sigmoidal dose-response model within Prism™ software.

Figure 4:
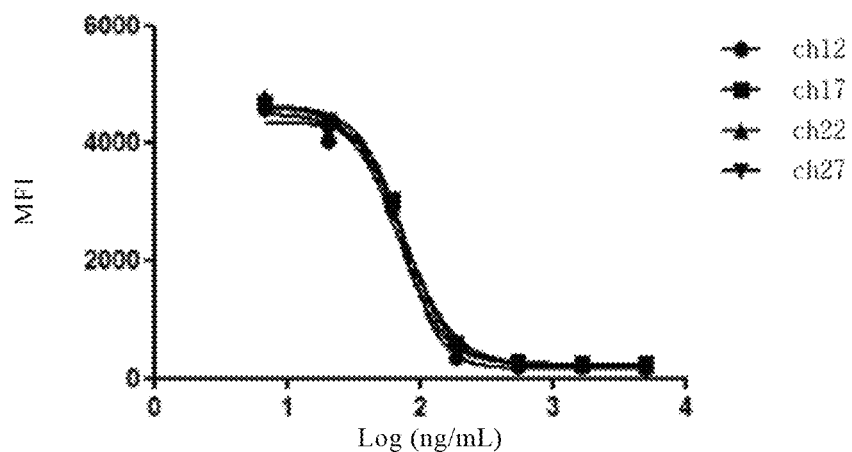
FIG. 4 shows the ability of chimeric antibodies to block the BTLA-HVEM binding.

The results are shown in FIG. 4 and Table 2 below. The chimeric antibodies ch12, ch17, ch22 and ch27 can effectively block the binding of human BTLA to HVEM on the cell surface.

TABLE 2

| Chimeric antibody | ch12 | ch17 | ch22 | ch27 |
|---|---|---|---|---|
| FACS, $IC_{50}$ (ng/mL) | 77.17 | 76.07 | 75.67 | 69.54 |

Example 9. Assay on the Effect of Chimeric Antibodies on T Cell Activity by Luciferase Reporter Gene T cell activation was achieved by stimulating T cell receptors (TCRs) that recognize specific peptides presented by major histocompatibility complex class I or class II proteins on antigen presenting cells (APCs). Then the activated TCRs initiated a cascade of signaling events that can be monitored by reporter genes driven by transcription factors (such as activator-protein-1 (AP-1), nuclear factor of activated T cells (NFAT), or nuclear factor κ-light-chain-enhancer of activated B cells (NFκb)). T cell responses were regulated by the composition or induction of engagement of expressed co-receptors on T cells. Programmed cell death protein (PD1) and BTLA are negative regulators of T cell activity. PD-1 and BTLA interact with their ligands (PD-L1) and HVEM, respectively, expressed on target cells including APC or cancer cells, which results in the delivery of an inhibitory signal by recruitment of phosphatase to the TCR signalosome, thereby producing inhibition of positive signaling. T cell signaling induced by the interaction between APC and T cells was measured by constructing two engineered stable cell lines, Jurkat cells (Jurkat/NFAT-Luc/hPD-1-hBTLA) and CHO cells (CHO/hPD-L1-hHVEM).

CHO cells stably expressing hPD-L1/hHVEM were spread on a 96-well plate at $5 \times 10^4$ cells/well, and incubated overnight at 37° C., 7% $CO_2$. After removing the cell supernatant, each well was added with 40 µL of chimeric anti-BTLA antibody diluent (initial concentration: 60 μg/mL, 3-fold titration), and 40 μL of Jurkat report cells capable of continuously expressing hPD-1/hBTLA/NFAT-luciferase, with the total cell number being 1×10$^5$ cells. The mixture was incubated for 6 hours at 37° C., 7% $CO_2$, and added with luciferase reagent. The luminescence values were detected by a microplate reader.

Figure 5:
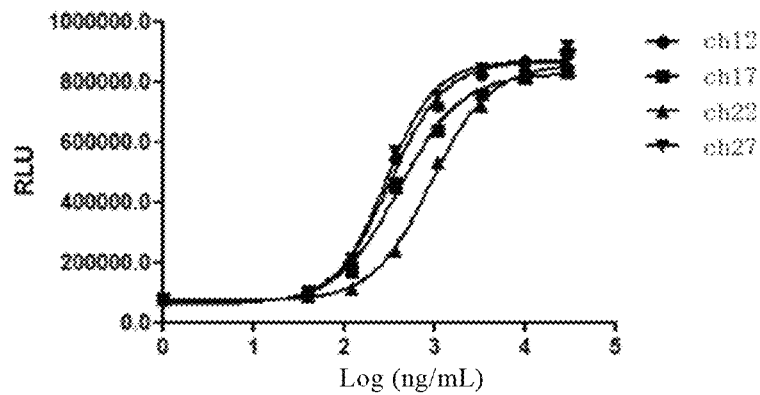
FIG. 5 shows an assay on the effect of chimeric antibodies on T cell activity.

The results are shown in FIG. 5 and Table 3 below. The chimeric antibodies ch12, ch17, ch22 and ch27 can significantly inhibit the T cell activity inhibition mediated by BTLA and PD-1.

TABLE 3

Effective promotion of T cell activity by chimeric antibodies

| Chimeric antibody | ch12 | ch17 | ch22 | ch27 |
|---|---|---|---|---|
| Luciferase, EC$_{50}$ (ng/ml) | 300.6 | 370.6 | 912.4 | 278.6 |

Example 10. Humanization of Antibodies

Humanization was carried out based on the variable region sequences of the antibodies secreted by the hybridoma cells obtained above. Briefly, the humanization comprised the following steps: A. comparing the gene sequence of the antibody secreted by each hybridoma cell with the gene sequence of the human embryonic antibody to find out a sequence with high homology; B. analyzing and inspecting HLA-DR affinity, and selecting a human embryonic framework sequence with low affinity; and C. analyzing the framework amino acid sequences of the variable regions and their periphery by using a computer simulation technology and applying molecular docking to investigate their spatial and stereo combination modes. The key amino acid individuals that can interact with hBTLA and maintain the spatial framework in the genetic sequence of the antibody secreted by each hybridoma cell were analyzed by calculating electrostatic force, Van der Waals' force, hydrophilcity and hydrophobicity, and entropy values, and grafted back into the selected human embryonic genetic framework. Then the amino acid sites of the framework region that must be preserved were mapped, and humanized antibodies were synthesized (Pini, A. et al., (1998) design and use of a phage display library: human antibodies with 10 subnanomolar affinity against a marker of angiogenesis eluted from a two-dimensional gel., *Journal of Biological Chemistry*, 273 (34): 21769-21776). Based on this, the following humanized antibodies were obtained: clones hu17, hu18 and hu19.

hu 17:
  Heavy chain amino acid sequence SEQ ID NO: 45;
  Light chain amino acid sequence SEQ ID NO: 46;
hu18:
  Heavy chain amino acid sequence SEQ ID NO: 45;
  Light chain amino acid sequence SEQ ID NO: 47;
hu19:
  Heavy chain amino acid sequence SEQ ID NO: 45;
  Light chain amino acid sequence SEQ ID NO: 48.

Example 11. Assay on the Binding of Humanized Antibodies to hBTLA by ELISA

The binding specificity of the humanized antibodies to hBTLA was determined by conventional ELISA method. A 96-well microplate was coated with 0.5 μg/mL hBTLA and incubated at 37° C. for 60 minutes. The solution in wells was then discarded, and the wells were washed 3 times with washing buffer, and blocked for 60 minutes with PBS containing 2% BSA. After being washed 3 times with washing buffer, the wells were added with gradiently-diluted antibodies, incubated at 37° C. for 60 minutes, and washed 3 times with washing buffer before adding a HRP-labeled mouse anti-human IgG4 secondary antibody diluted at 1:10000. The mixture was incubated at 37° C. for 1 hour, washed three times with washing buffer, and added with 100 μL of TMB substrate solution for color development at room temperature for 30 minutes, then the reaction was stopped with 100 μL of 2M hydrochloric acid solution and the absorbance was read at 450 nm.

Figure 6:
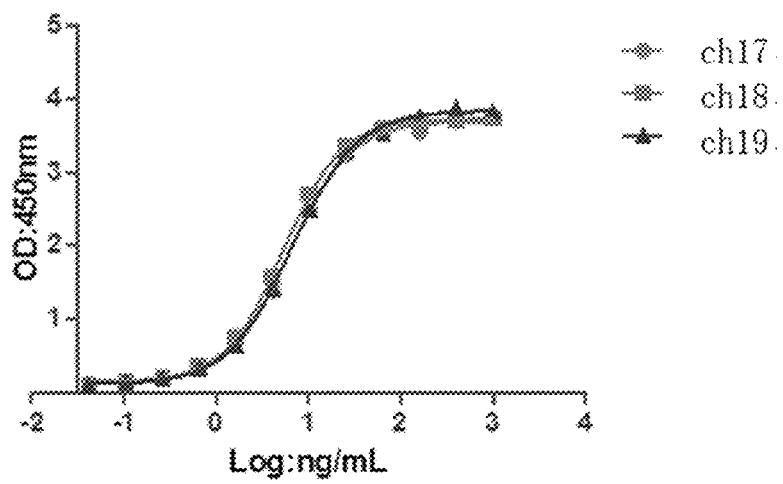
FIG. 6 shows an assay on the specific binding of humanized antibodies to BTLA.

The results are shown in FIG. 6. The humanized antibodies hu17, hu18, and hu19 can specifically bind to hBTLA. The EC$_{50}$ values are shown in Table 4 below.

TABLE 4

Data on the specific binding of humanized antibodies hu17, hu18 and hu19 to hBTLA

| Humanized antibody | hu17 | hu18 | hu19 |
|---|---|---|---|
| EC$_{50}$ (ng/mL) | 6.3 | 5.4 | 6.6 |

Example 12. Assay on the Binding of Humanized Antibodies to hBTLA on 293F Cells by FACS The humanized anti-BTLA antibodies were determined for their binding ability to hBTLA expressed on cells using cell-based flow cytometry (FACS). 293F cells expressing hBTLA were centrifuged and resuspended in an FACS buffer after digestion, and then added into a 96-well round-bottom plate at a density of 2.5×10$^{4/50}$ μL. Then the cells were mixed with 50 μL of antibody diluent at different concentrations (initial concentration: 10 μg/mL, 3-fold titration), and incubated at room temperature for 30 minutes. After being washed with an FACS buffer twice, the cells were added with 100 μL of goat anti-human IgG-PE antibody, incubated for 30 minutes away from light, and assayed by FACS after two washes with an FACS buffer. The washed cells were resuspended in 4° C. buffer containing propidium iodide (PI) and 0.02% sodium azide that prevents receptor internalization and analyzed by flow cytometry. Viable cells were gated on the basis of PI positive cells being excluded from the FSC/SSC gate and their geometric mean fluorescence intensity was measured. The data were analyzed using a sigmoidal dose-response model within Prism™ software.

Figure 7:
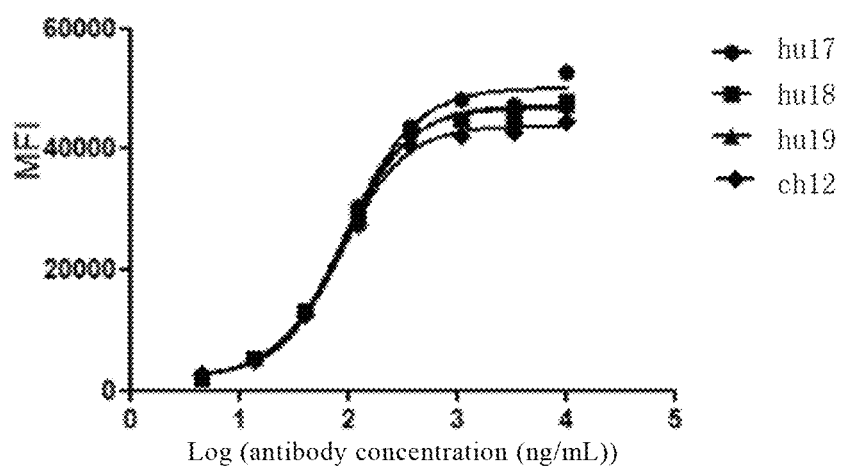
FIG. 7 shows an assay on the binding of humanized antibodies to hBTLA on 293F cells.

The results are shown in FIG. 7. The humanized antibodies hu17, hu18, and hu19 can effectively bind to hBTLA on 293 cells. The EC$_{50}$ values for each antibody are shown in Table 5 below.

TABLE 5

|  | hu17 | hu18 | hu19 | ch12 |
|---|---|---|---|---|
| EC50 (ng/ml) | 96.74 | 89.34 | 95.06 | 88.12 |

Example 13. Assay on Humanized Antibodies' Blocking of the Binding of BTLA to HVEM by FACS The humanized antibodies were determined for their ability to block the binding of hBTLA to hHVEM expressed on 293F cells using cell-based flow cytometry (FACS) assay.

hHVEM-293F stable cells were centrifuged and resuspended in an FACS buffer after digestion, and then added into a 96-well round-bottom plate at a density of $2.5×10^4$ cells/50 μL. Then the cells were mixed with previously biotin-labeled hBTLA (1 μg/mL) protein, incubated at 4° C. for 15 minutes, followed by mixing with 50 μL of humanized antibody diluent (initial concentration: 5 μg/mL, 3-fold titration) at different concentrations, and incubating at room temperature for 30 minutes. After being washed with an FACS buffer twice, the cells were added with 100 μL of goat anti-human IgG-PE antibody, incubated for 30 minutes away from light, and assayed by FACS after two washes with an FACS buffer. The washed cells were resuspended in 4° C. buffer containing propidium iodide (PI) and 0.02% sodium azide that prevents receptor internalization and analyzed by flow cytometry. Viable cells were gated on the basis of PI positive cells being excluded from the FSC/SSC gate and their geometric mean fluorescence intensity was measured. The data were analyzed using a sigmoidal dose-response model within Prism™ software.

Figure 8:
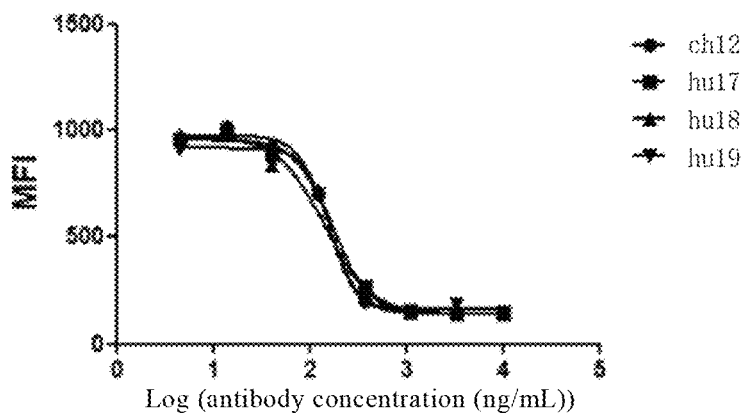
FIG. 8 shows an assay on humanized antibodies' blocking of the binding of BTLA to HVEM on the cell surface.

The results are shown in FIG. 8. The chimeric antibodies hu17, hu18, and hu19 can effectively block the binding of human BTLA to HVEM on the cell surface. The IC50 values for each antibody are shown in Table 6 below.

TABLE 6

|  | hu17 | hu18 | hu19 | ch12 |
| --- | --- | --- | --- | --- |
| IC50 (ng/ml) | 142.7 | 172.2 | 161.5 | 156.9 |

Example 14. Promotion of T Cell Activation by Humanized Anti-BTLA Antibodies

CHO cells stably expressing hPD-L1/hHVEM were spread on a 96-well plate at $5×10^4$ cells/well, and incubated overnight at 37° C., 7% $CO_2$. After removing the cell supernatant, each well was added with 40 μL of humanized anti-BTLA antibody diluent (initial concentration: 60 μg/mL, 3-fold gradient dilution), and 40 μL of Jurkat report cells capable of continuously expressing hPD-1/hBTLA/NFAT-luciferase, with the total cell number being $1×10^5$ cells. The mixture was incubated for 6 hours at 37° C., 7% $CO_2$, and added with luciferase reagent. The luminescence values were detected by a microplate reader.

Figure 9:
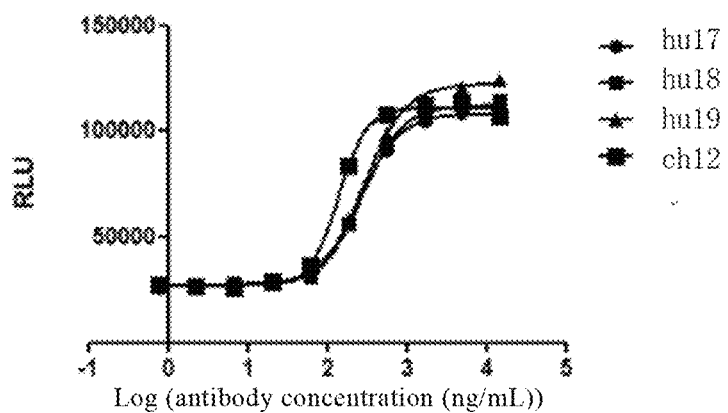
FIG. 9 shows an assay on humanized antibodies' promotion on T cell activation.

The results are shown in FIG. 9. The humanized anti-BTLA antibodies hu17 and hu18 can effectively promote T cell activation. The $EC_{50}$ values for each antibody are shown in Table 7 below.

TABLE 7

|  | hu17 | hu18 | hu19 | ch12 |
| --- | --- | --- | --- | --- |
| EC50 (ng/ml) | 256.7 | 277.3 | 290.4 | 138.7 |

Example 15. The Affinity of Humanized Anti-BTLA Antibodies for hBTLA

The assay was carried out using a Biacore T200 instrument (GE Healthcare). Series S CM5 chip was loaded on the instrument and the system buffer used was HBS-EP+(10 mM HEPES, pH 7.4, 150 mM NaCl, 3 mM EDTA, 0.05% surfactant P20). The BTLA-Fc antigens were coupled in a chip detection channel: injecting a mixed solution of 400 mM EDC and 100 mM NHS at 10 μL/min for 420 s to activate the surface of the chip, diluting the BTLA-Fc antigens in a 10 mM sodium acetate/acetic acid (pH 5.5) buffer to a final concentration of 20 μg/mL and injecting at 10 μL/min for coupling, and injecting a 1M ethanolamine-hydrochloric acid solution (pH 8.5) at 10 μL/min for 420 s for blocking.

Antibodies were diluted in a 2-fold gradient with Biacore system buffer for a total of 6 concentration points. Concentration gradients were 24 nM, 12 nM, 6 nM, 3 nM, 1.5 nM and 0.75 nM, with 24 nM being a replicate. Data were analyzed using Biacore T200 Evaluation Software (version no. 3.0, GE Healthcare). Data were fitted using a model of 1:1 Binding. The kinetic constants of the binding of the antibodies to the antigens, namely, the association rate constant ka (1/Ms), dissociation rate constant kd (1/s) and the affinity constant kd (M), were obtained by fitting, and the results are shown in Table 8.

TABLE 8

| Affinity data for humanized antibodies | | | |
| --- | --- | --- | --- |
|  | ka(1/Ms) | kd(1/s) | KD(M) |
| hu17 | 6.24E+05 | 1.16E−04 | 1.86E−10 |
| hu18 | 6.39E+05 | 8.67E−05 | 1.36E−10 |

Example 16. Characterization of Binding Kinetics of Humanized Antibodies to BTLAs of Different Species To detect cross-reactivity between chimeric antibodies and cynomolgus and murine BTLAs, Fortebio assay was used. Briefly, human BTLA, cynomolgus BTLA, or murine BTLA was coupled to an activated CM5 biosensor chip to achieve approximately 100-200 response units (RUs), and then the unreacted groups were blocked with 1M ethanolamine. Humanized antibody samples at increasing concentrations from 0.12 nM to 90 nM at 30 times were injected per minute into SPR running buffer and binding responses at BTLAs of different species were calculated by subtracting RU from the blank flow cell.

Figure 10:
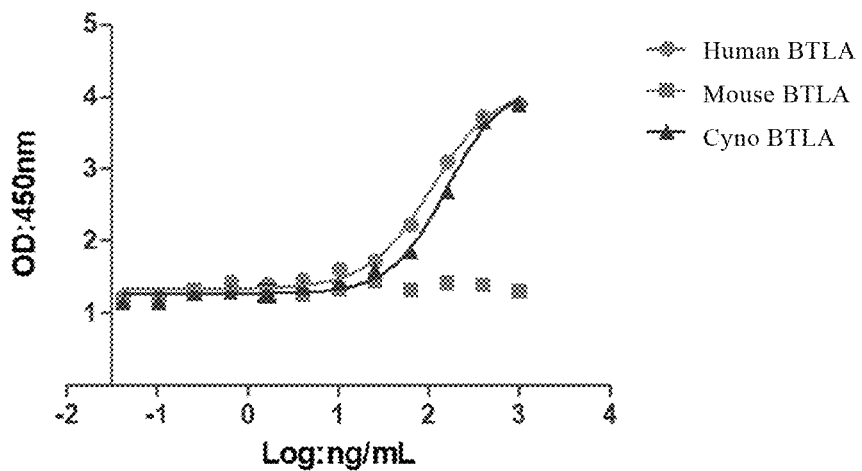
FIG. 10 shows a comparative experiment on the binding of humanized antibody 17 to BTLAs of different species.

The results are shown in FIG. 10. Comparative results of hu17's binding to BTLAs of different species show that: hu17 not only has high affinity for human BTLA, but also has similar affinity for cynomolgus monkey BTLA, and it barely binds to murine BTLA.

Example 17. Inhibition of Tumor Growth in Mice by Humanized Antibodies

The MC38-hHVME cell bank was created on MC38 cells (ATCC) by electroporating Hxp-hHVEM plasmids, the cells were subcloned by limiting dilution method, and the monoclones were screened by flow cytometry to acquire MC38-HVEM cells. The MC38-HVEM cells were inoculated into the right subcutaneous tissue of the humanized female B-HBTLA mice at 1×106 cells/0.1 mL, and when tumors grew to approximately 118 mm3, the mice were randomly grouped, by tumor volume, into 5 groups (8 mice per group), namely G1 0.9% sodium chloride injection solvent control group, G2 KLH (10 mg/kg) negative control group, G3 hu18 (1 mg/kg) group, G4 hu18 (3 mg/kg) group, and G5 hu18 (10 mg/kg) group. All groups were subjected to administration by intraperitoneal injection twice a week for 7 consecutive times, and the experiment ended 4 days after the last administration. Tumor volume and body weight of mice were measured and recorded twice a week. At the end of the experiment, animals were euthanized, tumors were taken, weighed, and photographed, and the relative tumor inhibition (TGITW %) was calculated.

Figure 11:
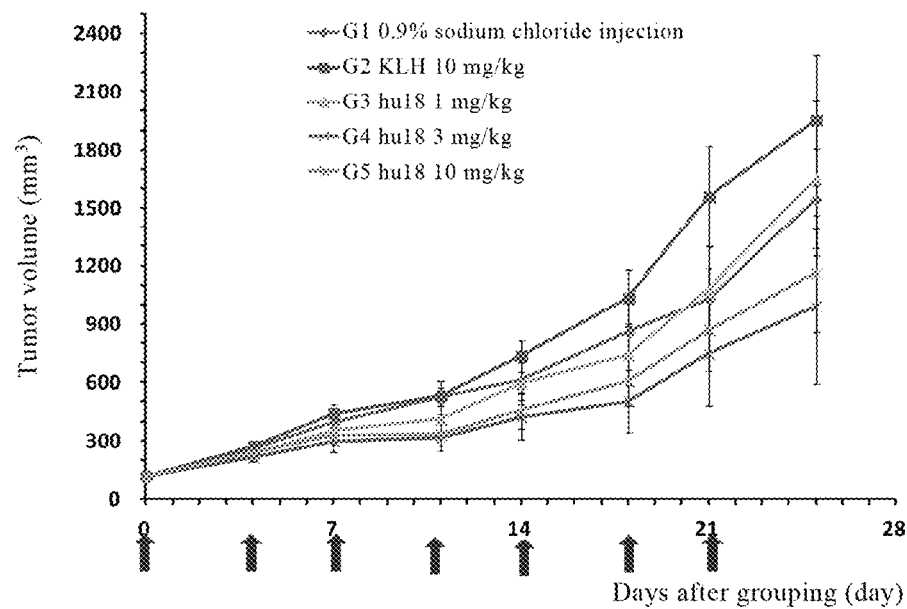
FIG. 11 shows the effect of hu18 on the tumor volume of MC38-hHVEM cell-transplanted B-hBTLA mice.

The effect of each sample on the tumor volume of MC38-hHVEM cell transplanted B-hBTLA mice is shown in Table 9 and FIG. 11. 21 days after the first administration, the KLH (10 mg/kg) negative control group had an mean tumor volume of 1560±256 mm3, and the other dosing groups had mean tumor volumes of 1073±224 mm3, 747±268 mm3 and 868±211 mm3, respectively. Compared with the KLH negative control group, the other dosing groups had the TGITV % of 33.7%, 56.4% and 48.0%, respectively, and P values of 0.175, 0.046 and 0.056, respectively, indicating that the test drug hu18 has a certain inhibitory effect on tumor growth at a dose level of 3 mg/kg.

TABLE 9

Effect of hu18 on tumor volume of MC38-hHVEM cell-transplanted B-hBTLA mice

| Group | Test drug | Tumor volume (mm³)[a] | | TGI (%) | P[b] |
|---|---|---|---|---|---|
| | | Before administration | 21 days after the first administration | | |
| G1 | 0.9% sodium chloride injection | 118 ± 2 | 1029 ± 155 | — | — |
| G2 | KLH (10 mg/kg) | 118 ± 2 | 1560 ± 256 | — | — |
| G3 | hu18 (1 mg/kg) | 118 ± 3 | 1073 ± 224 | 33.7 | 0.175 |
| G4 | JS004 (3 mg/kg) | 118 ± 2 | 747 ± 268 | 56.4 | 0.046 |
| G5 | JS004 (10 mg/kg) | 118 ± 3 | 868 ± 211 | 48.0 | 0.056 |

Note: a: mean±standard error; b: tumor volumes of the dosing groups compare statistically with that of the KLH negative control group 21 days after administration, t-test.

Figure 12:
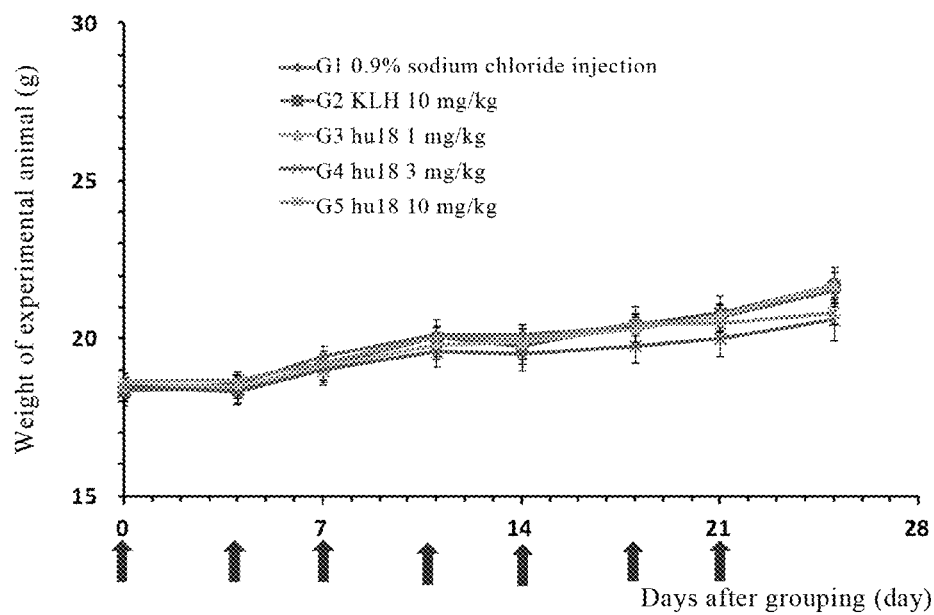
FIG. 12 shows the effect of samples on the body weight of MC38-hHVEM cell-transplanted B-hBTLA mice.

The results of the effect of each sample on the body weight of MC38-hHVEM cell-transplanted B-hBTLA mice are shown in Table 10 and FIG. 12. All experimental animals were well active and fed during administration, and the body weight of animals in each dosing group increased to some extent. No mortality of the experimental animals occurred during the experiment. Compared with the body weight of mice in the KLH negative control group, the body weight of the mice in each dosing group had no significant change (P>0.05) 21 days after the administration, indicating that the experimental animals have good tolerance to the samples.

TABLE 10

Effect of samples on the body weight of MC38-hHVEM cell-transplanted B-hBTLA mice

| Group | Test drug | Body weight (g)[a] | | P[b] | Body weight change (g) 21 days after administration |
|---|---|---|---|---|---|
| | | Before administration | 21 days after the first administration | | |
| G1 | 0.9% sodium chloride injection | 18.4 ± 0.4 | 20.7 ± 0.4 | — | +2.3 |
| G2 | KLH (10 mg/kg) | 18.3 ± 0.5 | 20.8 ± 0.6 | — | +2.5 |
| G3 | hu18 (1 mg/kg) | 18.5 ± 0.4 | 20.8 ± 0.4 | 0.943 | +2.3 |
| G4 | hu18 (3 mg/kg) | 18.5 ± 0.4 | 20.0 ± 0.6 | 0.341 | +1.5 |
| G5 | hu184 (10 mg/kg) | 18.6 ± 0.3 | 20.5 ± 0.2 | 0.623 | +1.9 |

Note:
[a]mean ± standard error;
[b]body weights of the dosing groups compared statistically with that of the KLH negative control group 21 days after administration, t-test.

Example 18. Humanized Antibody Hu18 without ADCC Effector Function

ADCC is initiated when an antibody binds to a cell surface target protein and then links to an Fc γ receptor (FcγR) expressed on effector cells. It is clearly documented that human IgG1 has significantly higher binding affinity for FcγR than IgG4, particularly for FcγR-I and FcγR-IIIA, which correlates with the strength of IgG1 to activate ADCC. In conjunction with ADCC, CDC is activated when antibodies cross-link the cell surface target and C1q protein, followed by a cascade reaction of complement complex formation and target cell lysis. As a proxy for ADCC and CDC, the detection of antibody binding to FcγR and C1q may serve as basic indicators of ADCC and CDC. Thus, in the present invention, the kinetic binding affinity of mAbs for major FcγRs was evaluated using biacore T200 (GE).

Anti-His antibody (GE) was immobilized on the sensor wafer. Various Fc receptors, including recombinant human FcγRIIIA (CD16a) V176, recombinant human FcγRIIA (CD32a) R167, recombinant human FcγRI (CD64) and recombinant human FcRn were captured, then a series of diluted recombinant human anti-BTLA antibodies (i.e., hu18) were injected, and the binding properties of the interactions were assayed and analyzed. hu18 is an IgG4 subtype, and hu18-IgG1 is an IgG1 subtype that shares the same Fab as hu18 and serves as a positive control.

As shown in Table 11, the binding of the recombinant human anti-BTLA antibody of the IgG4 subtype to Fc receptors was relatively weak compared to that of the control antibody of the IgG1 subtype, and the interaction of the hu18 antibody with FcγRIIIA (CD16a) V176 was 400-fold weaker compared to that of the control antibody of the IgG1 subtype. This suggests that hu18 has weak or no ADCC effect. As shown in Table 12, the hu18 antibody did not bind to C1q, while the hu18-IgG1 antibody was able to bind to C1q.

TABLE 11

The binding affinity of interaction between anti-BTLA antibodies and Fc receptors

| Fc receptor | Antibody | Ka (1/Ms) | Kd (1/s) | KD (M) |
|---|---|---|---|---|
| FcγRIIIA (CD16a)V176 | hu18-IgG1 | 6.15E+04 | 8.85E−03 | 1.44E−07 |
| | hu18 | N/A | N/A | 6.02E−05 |
| FcγRIIA (CD32a)R167 | hu18-IgG1 | N/A | N/A | 5.90E−06 |
| | hu18 | N/A | N/A | 4.06E−05 |
| FcγRI (CD64) | hu18-IgG1 | 2.99E+05 | 1.20E−03 | 4.00E−09 |
| | hu18 | 2.10E+05 | 3.87E−03 | 1.84E−08 |
| FcRn | hu18-IgG1 | 1.69E+06 | 3.88E−02 | 2.29E−08 |
| | hu18 | 5.12E+05 | 7.08E−02 | 1.38E−07 |

TABLE 12

The binding affinity of interaction between anti-BTLA antibodies and human C1q

| Protein | Antibody | Conclusion |
|---|---|---|
| C1q | hu18-IgG1 | Specific binding |
| | hu18 | Non-specific binding |

EMBODIMENTS

This disclosure includes the following nonlimiting embodiments: Embodiment 1. An isolated antibody or an antigen-binding fragment thereof, comprising: at least one light chain CDR domain selected from SEQ ID NOs: 7, 8, 9, 10, 11, 12, 16, 17, 18, 22, 23, 24, 31, 32 and 33, and/or at least one heavy chain CDR domain selected from SEQ ID NOs: 1, 2, 3, 4, 5, 6, 13, 14, 15, 19, 20, 21, 25, 26, 27, 28, 29 and 30.

Embodiment 2. The isolated antibody or the antigen-binding fragment thereof according to embodiment 1, wherein the light chain CDR of the isolated antibody or the antigen-binding fragment thereof comprises an LCDR1 selected from any one of CDR sequences set forth in SEQ ID NOs: 7, 10, 16, 22 and 31, an LCDR2 selected from any one of CDR sequences set forth in SEQ ID NOs: 8, 11, 17, 23 and 32, and/or an LCDR3 selected from any one of CDR sequences set forth in SEQ ID NOs: 9, 12, 18, 24 and 33; and/or the heavy chain CDR of the isolated antibody or the antigen-binding fragment thereof comprises an HCDR1 selected from any one of CDR sequences set forth in SEQ ID NOs: 1, 4, 13, 19, 25 and 28, an HCDR2 selected from any one of CDR sequences set forth in SEQ ID NOs: 2, 5, 14, 20, 26 and 29, and/or an HCDR3 selected from any one of CDR sequences set forth in SEQ ID NOs: 3, 6, 15, 21, 27 and 30.

Embodiment 3. The isolated antibody or the antigen-binding fragment thereof according to embodiment 2, wherein, in the light chain CDR of the isolated antibody or the antigen-binding fragment thereof, the LCDR1 is selected from any one of CDR sequences set forth in

| Group | LCDR1 | LCDR2 | LCDR3 |
|---|---|---|---|
| A | SEQ ID NO: 7 | SEQ ID NO: 8 | SEQ ID NO: 9 |
| B | SEQ ID NO: 10 | SEQ ID NO: 11 | SEQ ID NO: 12 |
| C | SEQ ID NO: 16 | SEQ ID NO: 17 | SEQ ID NO: 18 |
| D | SEQ ID NO: 22 | SEQ ID NO: 23 | SEQ ID NO: 24 |
| E | SEQ ID NO: 31 | SEQ ID NO: 32 | SEQ ID NO: 33 | and/or the amino acid sequences of the HCDR1, HCDR2 and HCDR3 of the heavy chain CDR of the isolated antibody or the antigen-binding fragment thereof are selected from any one of the following groups F-K:

| Group | HCDR1 | HCDR2 | HCDR3 |
|---|---|---|---|
| F | SEQ ID NO: 1 | SEQ ID NO: 2 | SEQ ID NO: 3 |
| G | SEQ ID NO: 4 | SEQ ID NO: 5 | SEQ ID NO: 6 |
| H | SEQ ID NO: 13 | SEQ ID NO: 14 | SEQ ID NO: 15 |
| I | SEQ ID NO: 19 | SEQ ID NO: 20 | SEQ ID NO: 21 |
| G | SEQ ID NO: 25 | SEQ ID NO: 26 | SEQ ID NO: 27 |
| K | SEQ ID NO: 28 | SEQ ID NO: 29 | SEQ ID NO: 30 |

Embodiment 5. The isolated antibody or the antigen-binding fragment thereof according to embodiment 1, wherein the amino acid sequences of the LCDR1, LCDR2 and LCDR3 of the light chain CDR and the amino acid sequences of the HCDR1, HCDR2 and HCDR3 of the heavy chain CDR of the isolated antibody or the antigen-binding fragment thereof are selected from any one of the following groups I-IX:

| Group | LCDR1 | LCDR2 | LCDR3 | HCDR1 | HCDR2 | HCDR3 |
|---|---|---|---|---|---|---|
| I | SEQ ID NO: 7 | SEQ ID NO: 8 | SEQ ID NO: 9 | SEQ ID NO: 1 | SEQ ID NO: 2 | SEQ ID NO: 3 |
| II | SEQ ID NO: 10 | SEQ ID NO: 11 | SEQ ID NO: 12 | SEQ ID NO: 4 | SEQ ID NO: 5 | SEQ ID NO: 6 |
| III | SEQ ID NO: 16 | SEQ ID NO: 17 | SEQ ID NO: 18 | SEQ ID NO: 13 | SEQ ID NO: 14 | SEQ ID NO: 15 |
| IV | SEQ ID NO: 22 | SEQ ID NO: 23 | SEQ ID NO: 24 | SEQ ID NO: 19 | SEQ ID NO: 20 | SEQ ID NO: 21 |
| V | SEQ ID NO: 22 | SEQ ID NO: 23 | SEQ ID NO: 24 | SEQ ID NO: 25 | SEQ ID NO: 26 | SEQ ID NO: 27 |
| VI | SEQ ID NO: 31 | SEQ ID NO: 32 | SEQ ID NO: 33 | SEQ ID NO: 28 | SEQ ID NO: 29 | SEQ ID NO: 30 |
| VII | SEQ ID NO: 7 | SEQ ID NO: 8 | SEQ ID NO: 9 | SEQ ID NO: 4 | SEQ ID NO: 5 | SEQ ID NO: 6 |
| VIII | SEQ ID NO: 10 | SEQ ID NO: 11 | SEQ ID NO: 12 | SEQ ID NO: 1 | SEQ ID NO: 2 | SEQ ID NO: 3 |
| IX | SEQ ID NO: 10 | SEQ ID NO: 11 | SEQ ID NO: 12 | SEQ ID NO: 13 | SEQ ID NO: 14 | SEQ ID NO: 15 |

SEQ ID NOs: 7, 10, 16, 22 and 31, the LCDR2 is selected from any one of CDR sequences set forth in SEQ ID NOs: 8, 11, 17, 23 and 32, and the LCDR3 is selected from any one of CDR sequences set forth in SEQ ID NOs: 9, 12, 18, 24 and 33; and/or in the heavy chain CDR of the isolated antibody or the antigen-binding fragment thereof, the HCDR1 is selected from any one of CDR sequences set forth in SEQ ID NOs: 1, 4, 13, 19, 25 and 28, the HCDR2 is selected from any one of CDR sequences set forth in SEQ ID NOs: 2, 5, 14, 20, 26 and 29, and the HCDR3 is selected from any one of CDR sequences set forth in SEQ ID NOs: 3, 6, 15, 21, 27 and 30.

Embodiment 4. The isolated antibody or the antigen-binding fragment thereof according to embodiment 2, wherein, the amino acid sequences of the LCDR1, LCDR2 and LCDR3 of the light chain CDR of the isolated antibody or the antigen-binding fragment thereof are selected from any one of the following group A-E:

Embodiment 6. The isolated antibody or the antigen-binding fragment thereof according to embodiment 1, comprising:

a light chain variable region having an amino acid sequence selected from any one of amino acid sequences set forth in SEQ ID NOs: 36, 37, 39, 41, 44, 46, 47 and 48; and/or a heavy chain variable region having an amino acid sequence selected from any one of amino acid sequences set forth in SEQ ID NOs: 34, 35, 38, 40, 42, 43 and 45.

Embodiment 7. The isolated antibody or the antigen-binding fragment thereof according to embodiment 6, wherein, the light chain variable region of the isolated antibody or the antigen-binding fragment thereof comprises an amino acid sequence set forth in SEQ ID NO: 36, and the heavy chain variable region comprises an amino acid sequence set forth in SEQ ID NO: 34 or 35;

the light chain variable region of the isolated antibody or the antigen-binding fragment thereof comprises an amino acid sequence set forth in SEQ ID NO: 37, and the heavy chain variable region comprises an amino acid sequence set forth in SEQ ID NO: 34 or 35;

the light chain variable region of the isolated antibody or the antigen-binding fragment thereof comprises an amino acid sequence set forth in SEQ ID NO: 39, and the heavy chain variable region comprises an amino acid sequence set forth in SEQ ID NO: 38;

the light chain variable region of the isolated antibody or the antigen-binding fragment thereof comprises an amino acid sequence set forth in SEQ ID NO: 41, and the heavy chain variable region comprises an amino acid sequence set forth in SEQ ID NO: 40 or 42;

the light chain variable region of the isolated antibody or the antigen-binding fragment thereof comprises an amino acid sequence set forth in SEQ ID NO: 44, and the heavy chain variable region comprises an amino acid sequence set forth in SEQ ID NO: 43; or the light chain variable region of the isolated antibody or the antigen-binding fragment thereof comprises an amino acid sequence set forth in SEQ ID NO: 46, 47 or 48, and the heavy chain variable region comprises an amino acid sequence set forth in SEQ ID NO: 45.

Embodiment 8. The isolated antibody or the antigen-binding fragment thereof according to any one of embodiments 1-7, wherein the antibody is a chimeric antibody, a humanized antibody or a fully human antibody.

Embodiment 9. An isolated nucleic acid, selected from:
(1) a polynucleotide sequence encoding the isolated antibody or the antigen-binding fragment thereof according to any one of embodiments 1-7; and
(2) a complementary sequence of the polynucleotide sequence of (1).

Embodiment 10. An expression vector or a host cell comprising the expression vector, wherein the expression vector comprises the isolated nucleic acid according to embodiment 9.

Embodiment 11. A pharmaceutical composition comprising the isolated antibody or the antigen-binding fragment thereof according to any one of embodiments 1-7, the nucleic acid according to embodiment 9, the expression vector or host cell according to embodiment 10, or any combination thereof.

Embodiment 12. Use of the isolated antibody or the antigen-binding fragment thereof according to any one of embodiments 1-7, the nucleic acid according to embodiment 9, or the expression vector or host cell according to embodiment 10 in preparing a medicament for treating or preventing BTLA-mediated diseases.

Embodiment 13. An immunoconjugate comprising the antibody or the antigen-binding fragment thereof according to any one of embodiments 1-7 conjugated with a therapeutic agent, preferably the therapeutic agent being a toxin, a radioisotope, a medicament, or a cytotoxic agent.

What is claimed is:

1. An isolated anti-BTLA antibody or an antigen-binding fragment thereof wherein the amino acid sequences of the LCDR1, LCDR2 and LCDR3 of the light chain CDR and the amino acid sequences of the HCDR1, HCDR2 and HCDR3 of the heavy chain CDR of the isolated antibody or the antigen-binding fragment thereof are selected from any one of the following groups I-IX:

| Group | LCDR1 | LCDR2 | LCDR3 |
|---|---|---|---|
| I | SEQ ID NO: 7 | SEQ ID NO: 8 | SEQ ID NO: 9 |
| II | SEQ ID NO: 10 | SEQ ID NO: 11 | SEQ ID NO: 12 |
| III | SEQ ID NO: 16 | SEQ ID NO: 17 | SEQ ID NO: 18 |
| IV | SEQ ID NO: 22 | SEQ ID NO: 23 | SEQ ID NO: 24 |
| V | SEQ ID NO: 22 | SEQ ID NO: 23 | SEQ ID NO: 24 |
| VI | SEQ ID NO: 31 | SEQ ID NO: 32 | SEQ ID NO: 33 |
| VII | SEQ ID NO: 7 | SEQ ID NO: 8 | SEQ ID NO: 9 |
| VIII | SEQ ID NO: 10 | SEQ ID NO: 11 | SEQ ID NO: 12 |
| IX | SEQ ID NO: 10 | SEQ ID NO: 11 | SEQ ID NO: 12 |

| Group | HCDR1 | HCDR2 | HCDR3 |
|---|---|---|---|
| I | SEQ ID NO: 1 | SEQ ID NO: 2 | SEQ ID NO: 3 |
| II | SEQ ID NO: 4 | SEQ ID NO: 5 | SEQ ID NO: 6 |
| III | SEQ ID NO: 13 | SEQ ID NO: 14 | SEQ ID NO: 15 |

-continued

| IV | SEQ ID NO: 19 | SEQ ID NO: 20 | SEQ ID NO: 21 |
| V | SEQ ID NO: 25 | SEQ ID NO: 26 | SEQ ID NO: 27 |
| VI | SEQ ID NO: 28 | SEQ ID NO: 29 | SEQ ID NO: 30 |
| VII | SEQ ID NO: 4 | SEQ ID NO: 5 | SEQ ID NO: 6 |
| VIII | SEQ ID NO: 1 | SEQ ID NO: 2 | SEQ ID NO: 3 |
| IX | SEQ ID NO: 13 | SEQ ID NO: 14 | SEQ ID NO: 15. |

2. The anti-BTLA antibody or the antigen-binding fragment thereof according to claim 1, comprising:
   a light chain variable region having an amino acid sequence selected from any one of amino acid sequences set forth in SEQ ID NOs: 36, 37, 39, 41, 44, 46, 47 and 48; and
   a heavy chain variable region having an amino acid sequence selected from any one of amino acid sequences set forth in SEQ ID NOs: 34, 35, 38, 40, 42, 43 and 45.

3. The anti-BTLA antibody or the antigen-binding fragment thereof according to claim 2, wherein,
   the light chain variable region of the isolated antibody or the antigen-binding fragment thereof comprises an amino acid sequence set forth in SEQ ID NO: 36, and the heavy chain variable region comprises an amino acid sequence set forth in SEQ ID NO: 34 or 35;
   the light chain variable region of the isolated antibody or the antigen-binding fragment thereof comprises an amino acid sequence set forth in SEQ ID NO: 37, and the heavy chain variable region comprises an amino acid sequence set forth in SEQ ID NO: 34 or 35;
   the light chain variable region of the isolated antibody or the antigen-binding fragment thereof comprises an amino acid sequence set forth in SEQ ID NO: 39, and the heavy chain variable region comprises an amino acid sequence set forth in SEQ ID NO: 38;
   the light chain variable region of the isolated antibody or the antigen-binding fragment thereof comprises an amino acid sequence set forth in SEQ ID NO: 41, and the heavy chain variable region comprises an amino acid sequence set forth in SEQ ID NO: 40 or 42;
   the light chain variable region of the isolated antibody or the antigen-binding fragment thereof comprises an amino acid sequence set forth in SEQ ID NO: 44, and the heavy chain variable region comprises an amino acid sequence set forth in SEQ ID NO: 43; or
   the light chain variable region of the isolated antibody or the antigen-binding fragment thereof comprises an amino acid sequence set forth in SEQ ID NO: 46, 47 or 48, and the heavy chain variable region comprises an amino acid sequence set forth in SEQ ID NO: 45.

4. The anti-BTLA antibody or the antigen-binding fragment thereof according to claim 1, wherein the antibody is a chimeric antibody, or a humanized antibody.

5. An isolated nucleic acid molecule, comprising (1) a polynucleotide sequence encoding the anti-BTLA antibody or the antigen-binding fragment thereof according to claim 1, and (2) a complementary sequence of the polynucleotide sequence of (1).

6. The isolated nucleic acid molecule of claim 5, wherein the light chain variable region of the antibody or the antigen-binding fragment thereof comprises an amino acid sequence as set forth in SEQ ID NO: 46, 47 or 48; and the heavy chain variable region of the antibody or the antigen-binding fragment thereof comprises an amino acid sequence as set forth in SEQ ID NO: 45.

7. An expression vector comprising the isolated nucleic acid molecule according to claim 5.

8. The expression vector of claim 7 comprising the nucleic acid molecule encoding an antibody comprising a heavy chain variable region selected from the amino acid sequence of SEQ ID NO: 45, and a light chain variable region selected from the group consisting of the amino acid sequence of SEQ ID NO: 46, SEQ ID NO: 47 and SEQ ID NO: 48, or an antigen-binding fragment thereof.

9. A host cell comprising the nucleic acid molecule according to claim 5.

10. The host cell of claim 9 comprising the nucleic acid molecule encoding an antibody comprising a heavy chain variable region selected from the amino acid sequence of SEQ ID NO: 45, and a light chain variable region selected from the group consisting of the amino acid sequence of SEQ ID NO: 46, SEQ ID NO: 47 and SEQ ID NO: 48, or an antigen-binding fragment thereof.

11. A pharmaceutical composition comprising the anti-BTLA antibody or the antigen-binding fragment thereof according to claim 1, a nucleic acid molecule encoding the antibody or the antigen-binding fragment thereof, an expression vector comprising the nucleic acid molecule, or a host cell comprising the nucleic acid molecule or the expression vector, or any combination thereof; and a pharmaceutically acceptable carrier.

12. A method for treating a BTLA-mediated disease by eliminating, inhibiting, or reducing BTLA activity, comprising administering to a subject in need thereof a therapeutically effective amount of antibodies or the antigen-binding fragments thereof of claim 1, or an nucleic acid molecule encoding the antibody or the antigen-binding fragment thereof, an expression vector comprising the nucleic acid molecule, or a host cell comprising the nucleic acid molecule or the expression vector, an immunoconjugate comprising the antibody an antigen-binding fragment thereof, or a pharmaceutical composition comprising the antibody or the antigen-binding fragment thereof, the expression vector, the host cell or the immunoconjugate, wherein the BTLA-mediated disease is a cancer.

13. An immunoconjugate comprising the antibody or an antigen-binding fragment thereof according to claim 1 conjugated with a therapeutic agent.

14. The immunoconjugate of claim 13, wherein the antibody comprises a heavy chain variable region selected from the amino acid sequence of SEQ ID NO: 45, and a light chain variable region selected from the group consisting of the amino acid sequence of SEQ ID NO: 46, SEQ ID NO: 47 and SEQ ID NO: 48.

15. The immunoconjugate of claim 13, wherein the therapeutic agent is a toxin, a radioisotope, or a cytotoxic agent.

* * * * *